(12) United States Patent
Hammack et al.

(10) Patent No.: US 9,597,100 B2
(45) Date of Patent: Mar. 21, 2017

(54) ARTICULATING BASKET WITH SIMULTANEOUS BASKET EXTENSION OR BASKET RETRACTION

(71) Applicant: Cook Medical Technologies LLC, Bloomington, IN (US)

(72) Inventors: Anthony D. Hammack, Bloomington, IN (US); Walter N. Ryan, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 59 days.

(21) Appl. No.: 14/068,517

(22) Filed: Oct. 31, 2013

(65) Prior Publication Data

US 2014/0058404 A1 Feb. 27, 2014

Related U.S. Application Data

(62) Division of application No. 11/591,376, filed on Nov. 1, 2006, now Pat. No. 8,597,303.
(Continued)

(51) Int. Cl.
*A61B 17/221* (2006.01)
*A61B 10/04* (2006.01)
(Continued)

(52) U.S. Cl.
CPC ............ *A61B 17/221* (2013.01); *A61B 10/04* (2013.01); *A61B 17/29* (2013.01);
(Continued)

(58) Field of Classification Search
CPC ............ A61B 17/221; A61B 2017/003; A61B 2017/2212; A61B 2017/2902;
(Continued)

(56) References Cited

U.S. PATENT DOCUMENTS 2,137,710 A 11/1938 Anderson
4,256,113 A * 3/1981 Chamness ...................... 606/47
(Continued)

FOREIGN PATENT DOCUMENTS

DE DT 2428319 A1 1/1976
EP 0446020 B1 1/1995
(Continued)

OTHER PUBLICATIONS

International Search Report from PCT application No. PCT/US2006/042637 dated Mar. 6, 2007 (6 pages).
(Continued)

*Primary Examiner* — Melanie Tyson
*Assistant Examiner* — Tin Nguyen
(74) *Attorney, Agent, or Firm* — Brinks Gilson & Lione

(57) ABSTRACT

A retrieval device is provided for retrieving stones, calculi, and other objects from a body. The device allows for a retrieval basket to be articulated and extended simultaneously. The device also allows for the basket to be articulated and retracted simultaneously. The device comprises a body, an articulator movably connected to the body, a first wire and a second wire having distal ends, and a tool formed by the distal ends of the first wire and the second wire.

11 Claims, 24 Drawing Sheets

Related U.S. Application Data

(60) Provisional application No. 60/732,929, filed on Nov. 3, 2005.

(51) Int. Cl.
*A61B 17/00* (2006.01)
*A61B 17/29* (2006.01)

(52) U.S. Cl.
CPC . *A61B 2017/003* (2013.01); *A61B 2017/2212* (2013.01); *A61B 2017/291* (2013.01); *A61B 2017/292* (2013.01); *A61B 2017/2902* (2013.01); *A61B 2017/2911* (2013.01); *A61B 2017/2915* (2013.01); *A61B 2017/2916* (2013.01); *A61B 2017/2922* (2013.01); *A61B 2017/2923* (2013.01); *A61B 2017/2927* (2013.01)

(58) Field of Classification Search
CPC ...... A61B 2017/291; A61B 2017/2911; A61B 17/29; A61B 10/04; A61B 2017/2915; A61B 2017/2922; A61B 2017/2927; A61B 2017/292; A61B 2017/2923; A61B 2017/2916
USPC ..................... 606/113, 114, 110, 127, 42, 47
See application file for complete search history.

(56) References Cited

U.S. PATENT DOCUMENTS

| | | |
|---|---|---|
| 4,393,872 A | 7/1983 | Reznik et al. |
| 4,763,668 A | 8/1988 | Macek et al. |
| 4,872,456 A | 10/1989 | Hasson |
| 4,968,678 A | 11/1990 | Ornstein |
| 5,057,114 A | 10/1991 | Wittich et al. |
| 5,064,428 A | 11/1991 | Cope et al. |
| 5,197,968 A | 3/1993 | Clement |
| 5,254,088 A | 10/1993 | Lundquist et al. |
| 5,290,294 A | 3/1994 | Cox et al. |
| 5,308,357 A | 5/1994 | Lichtman |
| 5,308,358 A | 5/1994 | Bond et al. |
| 5,318,040 A | 6/1994 | Kensey et al. |
| 5,318,589 A | 6/1994 | Lichtman |
| 5,330,482 A | 7/1994 | Gibbs et al. |
| 5,358,508 A | 10/1994 | Cobb et al. |
| 5,376,094 A | 12/1994 | Kline |
| 5,387,219 A | 2/1995 | Rappe |
| 5,496,330 A | 3/1996 | Bates et al. |
| 5,556,376 A | 9/1996 | Yoon |
| 5,643,282 A | 7/1997 | Kieturakis |
| 5,788,710 A | 8/1998 | Bates et al. |
| 5,906,622 A | 5/1999 | Lippitt et al. |
| 5,989,266 A | 11/1999 | Foster |
| 6,071,281 A | 6/2000 | Burnside et al. |
| 6,099,534 A | 8/2000 | Bates et al. |
| 6,159,220 A | 12/2000 | Gobron et al. |
| 6,162,209 A | 12/2000 | Gobron et al. |
| 6,168,603 B1 | 1/2001 | Leslie et al. |
| 6,174,318 B1 | 1/2001 | Bates et al. |
| 6,183,482 B1 | 2/2001 | Bates et al. |
| 6,203,552 B1 | 3/2001 | Bagley et al. |
| 6,217,589 B1 | 4/2001 | McAlister |
| 6,224,612 B1 | 5/2001 | Bates et al. |
| 6,258,101 B1 * | 7/2001 | Blake, III ............ A61B 17/221 606/113 |
| 6,264,664 B1 | 7/2001 | Avellanet |
| 6,280,451 B1 | 8/2001 | Bates et al. |
| 6,302,895 B1 | 10/2001 | Gobron et al. |
| 6,342,062 B1 | 1/2002 | Suon et al. |
| 6,348,056 B1 | 2/2002 | Bates et al. |
| 6,350,266 B1 | 2/2002 | White et al. |
| 6,368,328 B1 | 4/2002 | Chu et al. |
| 6,368,338 B1 | 4/2002 | Konya et al. |
| 6,383,196 B1 | 5/2002 | Leslie et al. |
| 6,402,761 B2 | 6/2002 | McAlister |
| 6,464,710 B1 | 10/2002 | Foster |
| 6,491,698 B1 | 12/2002 | Bates et al. |
| 6,500,182 B2 | 12/2002 | Foster |
| 6,520,968 B2 | 2/2003 | Bates et al. |
| 6,527,781 B2 | 3/2003 | Bates et al. |
| 6,544,227 B2 | 4/2003 | Sahatjian et al. |
| 6,565,530 B2 | 5/2003 | Sahatjian et al. |
| 6,602,262 B2 | 8/2003 | Griego et al. |
| 6,626,915 B2 | 9/2003 | Leveillee |
| 6,652,537 B2 | 11/2003 | Mercereau et al. |
| 6,676,668 B2 | 1/2004 | Mercereau et al. |
| 6,692,484 B1 | 2/2004 | Karpiel et al. |
| 6,720,402 B2 | 4/2004 | Langer et al. |
| 6,730,097 B2 | 5/2004 | Dennis |
| 6,893,450 B2 | 5/2005 | Foster |
| 7,041,108 B2 | 5/2006 | Lippitt et al. |
| 7,241,299 B2 | 7/2007 | Gerard |
| 2003/0004538 A1 * | 1/2003 | Secrest et al. ................. 606/200 |
| 2003/0109874 A1 | 6/2003 | Dennis |
| 2004/0092957 A1 * | 5/2004 | Lippitt ................. A61B 17/221 606/127 |
| 2004/0122445 A1 | 6/2004 | Butler et al. |
| 2004/0133213 A1 | 7/2004 | Bagley et al. |

FOREIGN PATENT DOCUMENTS

| | | |
|---|---|---|
| EP | 0 512 729 B1 | 7/1995 |
| EP | 0538984 B1 | 3/1997 |
| EP | 0679071 B1 | 3/1999 |
| EP | 1348381 A2 | 10/2003 |
| WO | WO 9604875 A1 | 2/1996 |
| WO | WO 9605773 A1 | 2/1996 |
| WO | WO 9717014 A1 | 5/1997 |
| WO | WO 9738632 A1 | 10/1997 |
| WO | WO 9742884 A2 | 11/1997 |
| WO | WO 0071036 A2 | 11/2000 |
| WO | WO 0180748 A2 | 11/2001 |
| WO | WO 03/049625 A1 | 6/2003 |

OTHER PUBLICATIONS

International Preliminary Report on Patentability, corresponding PCT Application No. PCT/US2006/042637, dated May 15, 2008.
Canadian Examination Report dated Dec. 20, 2007 for corresponding Canadian Application No. 2,500,853, dated Dec. 20, 2007.
Canadian Office Action, issued in 2,626,867, dated Dec. 3, 2009.
Hoffman, Nathan et al., "Percutaneous Renal Stone Extraction: In Vitro Study of Retrieval Devices," The Journal of Urology, Copyright © 2004 by American Urological Association, vol. 172, Aug. 2004, pp. 559-561.
EP Invitation dated Jun. 9, 2015 for corresponding European Application No. 06827269.9, dated Nov. 1, 2006.

* cited by examiner

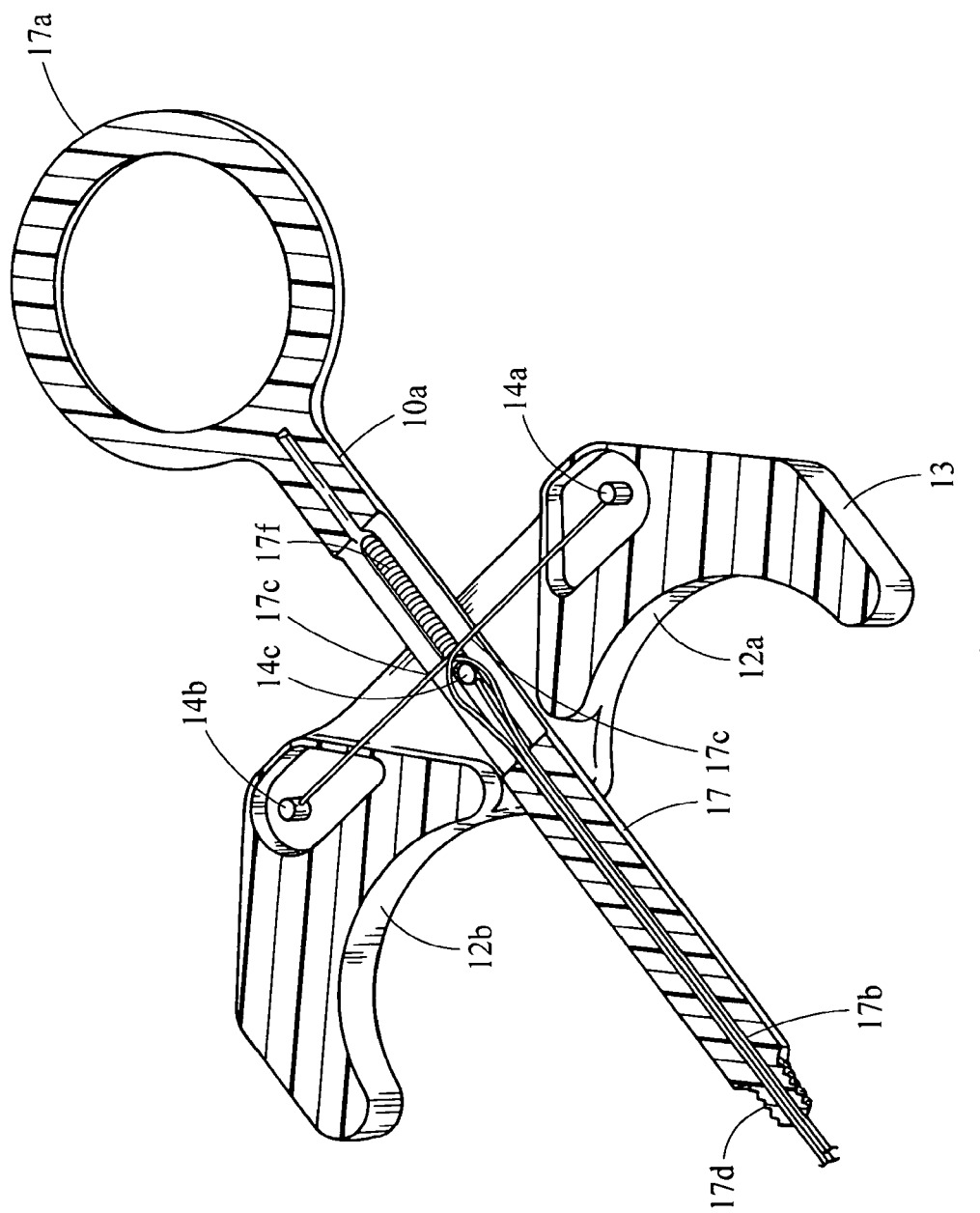

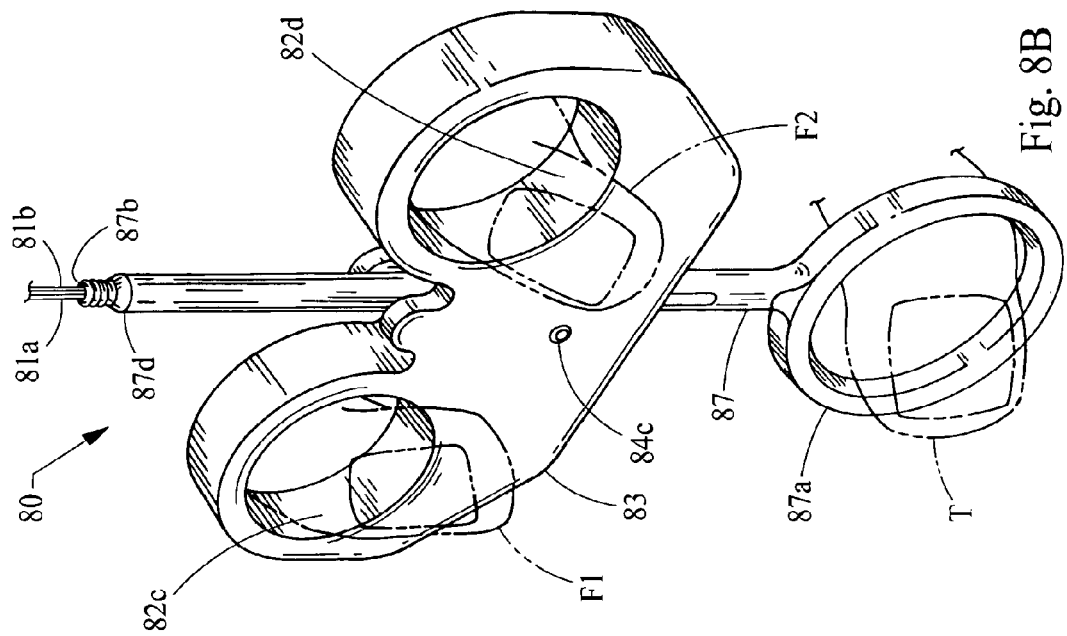
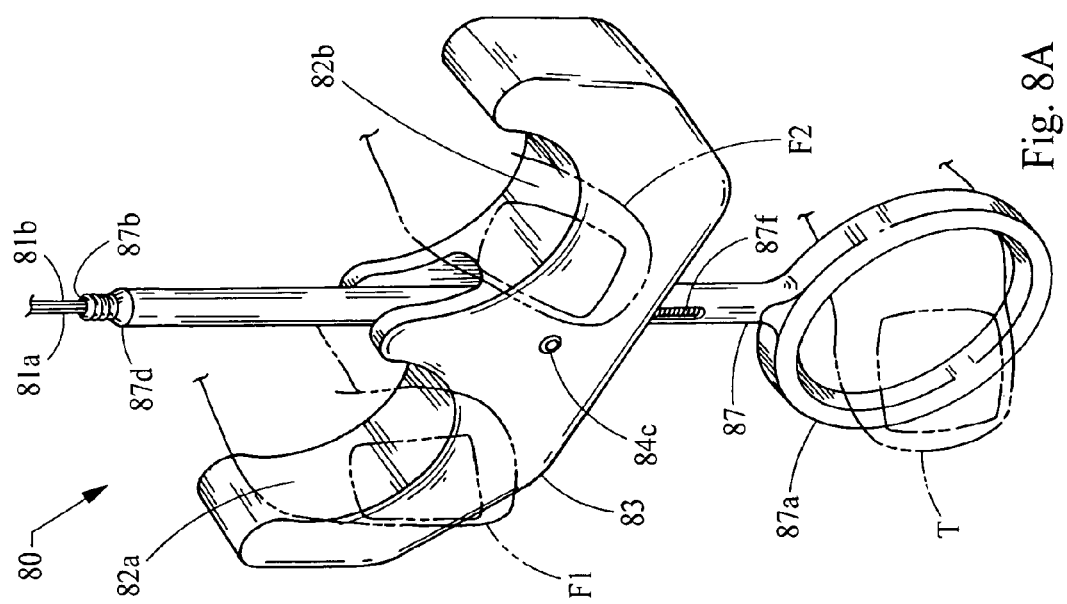

ARTICULATING BASKET WITH SIMULTANEOUS BASKET EXTENSION OR BASKET RETRACTION

RELATED APPLICATIONS

This application is a divisional application of U.S. application Ser. No. 11/591,376, filed Nov. 1, 2006, which claims the benefit of U.S. Provisional Application No. 60/732,929, filed Nov. 3, 2005, the entire contents of which are hereby incorporated herein by reference.

FIELD OF THE INVENTION

This invention relates to medical retrieval devices used in minimally invasive surgery, particularly those used to retrieve stones and calculi from a patient.

BACKGROUND OF THE INVENTION

Stone retrieval devices are often employed in order to remove a stone from a ureter or kidney. Removal of a stone from a ureter or kidney is a difficult process because the area within which the medical professional works is small and narrow. Often a stone is not located directly in front of the retrieval basket. The location of the stone makes it difficult to retrieve. In an attempt to retrieve the object, the medical professional will attempt to bend the basket, causing the basket to bend-over partially onto itself. This movement will allow one side of the basket to expand and be more open than the opposite side. When the basket is at least partially bent-over on itself, the medical professional will attempt to maneuver the basket so that it encapsulates the object. However, the basket cannot be extended or retracted while bent. Thus, stones that are not directly in front of the device cannot be easily captured.

The medical professional has little control of the basket because the basket cannot be bent while being extended or retracted. Thus, during the interim period between when the basket surrounds the stone and when the basket is retracted, the stone can shift, move, or dislodge, making the capture attempt a failure, causing the medical professional to start the procedure over.

BRIEF SUMMARY OF THE INVENTION

A medical device is provided. The device includes a body, an articulator movably connected to the body, and at least a first and a second wire having distal ends. The first and second wire is in communication with the articulator. The device further includes a tool disposed at the distal end of the first and second wire, wherein the articulator is capable of moving the tool outside the longitudinal plane, and wherein the tool is capable of being extended and retracted in a longitudinal plane simultaneously with movement outside the longitudinal plane.

Further, a medical device is provided. The device includes a body, a slide assembly slideably attached to the body, and an articulator rotateably attached to the body. The articulator is in communication with the slide assembly. The device further includes a first wire and a second wire having distal ends, wherein the first wire and the second wire are attached to the articulator. The device further includes a tool disposed at the distal ends of the first and second wires, wherein the articulator is configured to move the tool outside a longitudinal plane, and wherein the slide assembly is configured to extend and retract the first and second wires.

Further, a medical device is provided. The device includes a tool formed by at least one wire. The device further includes means for extending or retracting the tool and simultaneously articulating the tool in a plane outside a longitudinal plane.

Further, a method for retrieving an object is provided. The method includes inserting a device for removing an object into a patient, extending a tool of the device out to the object, and articulating the tool to encapsulate the object. The method further includes retracting the tool to retrieve the object, wherein the extending and the articulating are capable of being performed simultaneously or the articulating and the retracting are capable of being performed simultaneously.

BRIEF DESCRIPTION OF THE SEVERAL VIEWS OF THE DRAWINGS

The embodiments will be further described in connection with the attached drawing figures. It is intended that the drawings included as a part of this specification be illustrative of the embodiments and should in no way be considered as a limitation on the scope of the invention.

FIGS. 1A, 1B-1C show partial cross-sectional views of an embodiment of the device;

FIGS. 8A-8B are isometric views of the proximal portion of embodiments of the device;

DETAILED DESCRIPTION OF PRESENTLY PREFERRED EMBODIMENTS

The device provides a way to simultaneously articulate and extend a retrieval basket and also to simultaneously articulate and retract the basket for retrieving stones, calculi, and other objects from a patient. The use of the device is not limited to use in human patients; the device has veterinary and non-medical uses including but not limited to retrieving objects from any hard-to-reach area. A more detailed description of the embodiments will now be given with reference to FIGS. 1-18. The present invention is not limited to those embodiments illustrated; it specifically contemplates other embodiments not illustrated but intended to be included in the claims.

Figure 1A:
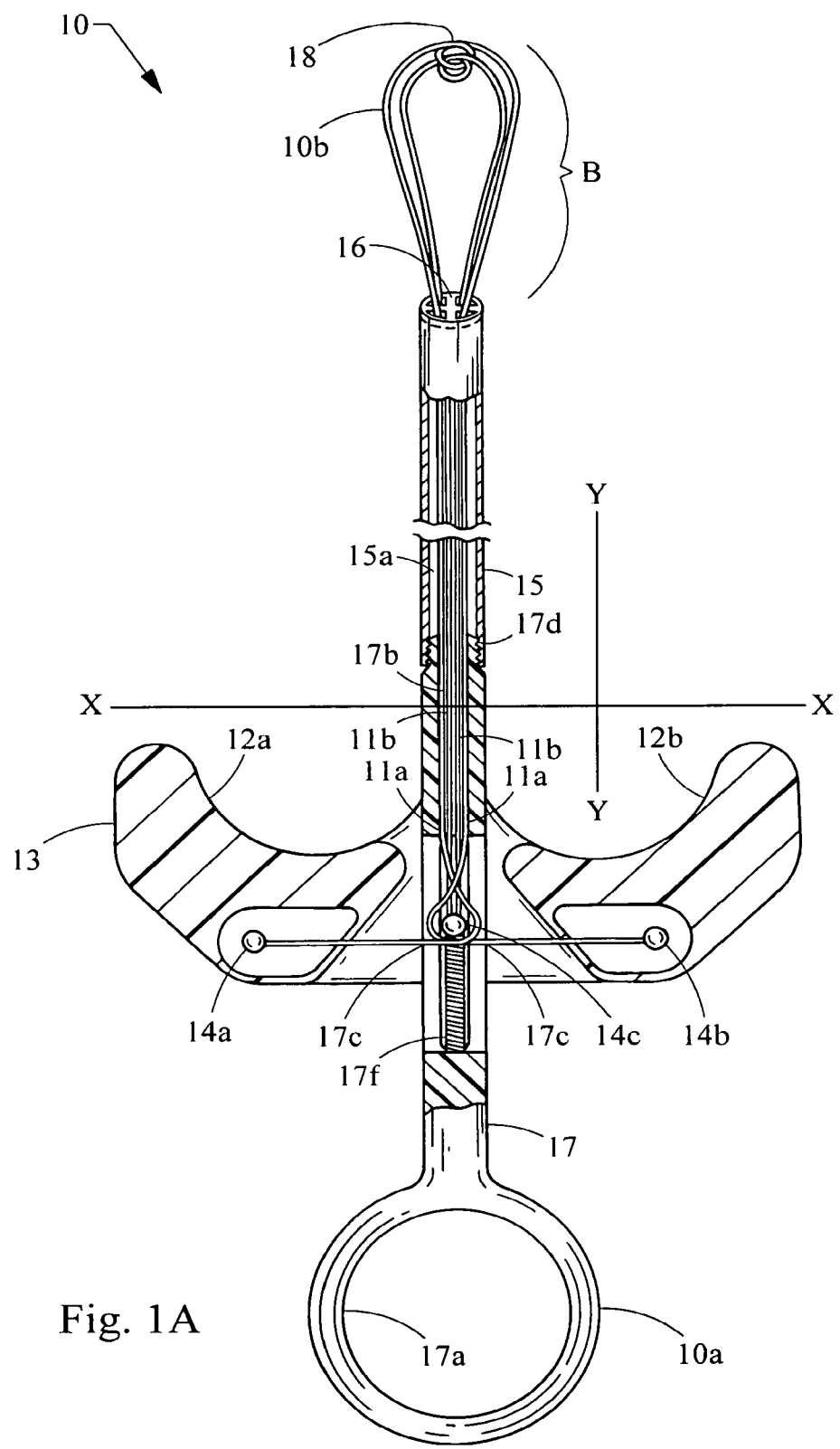
Figure 1B:
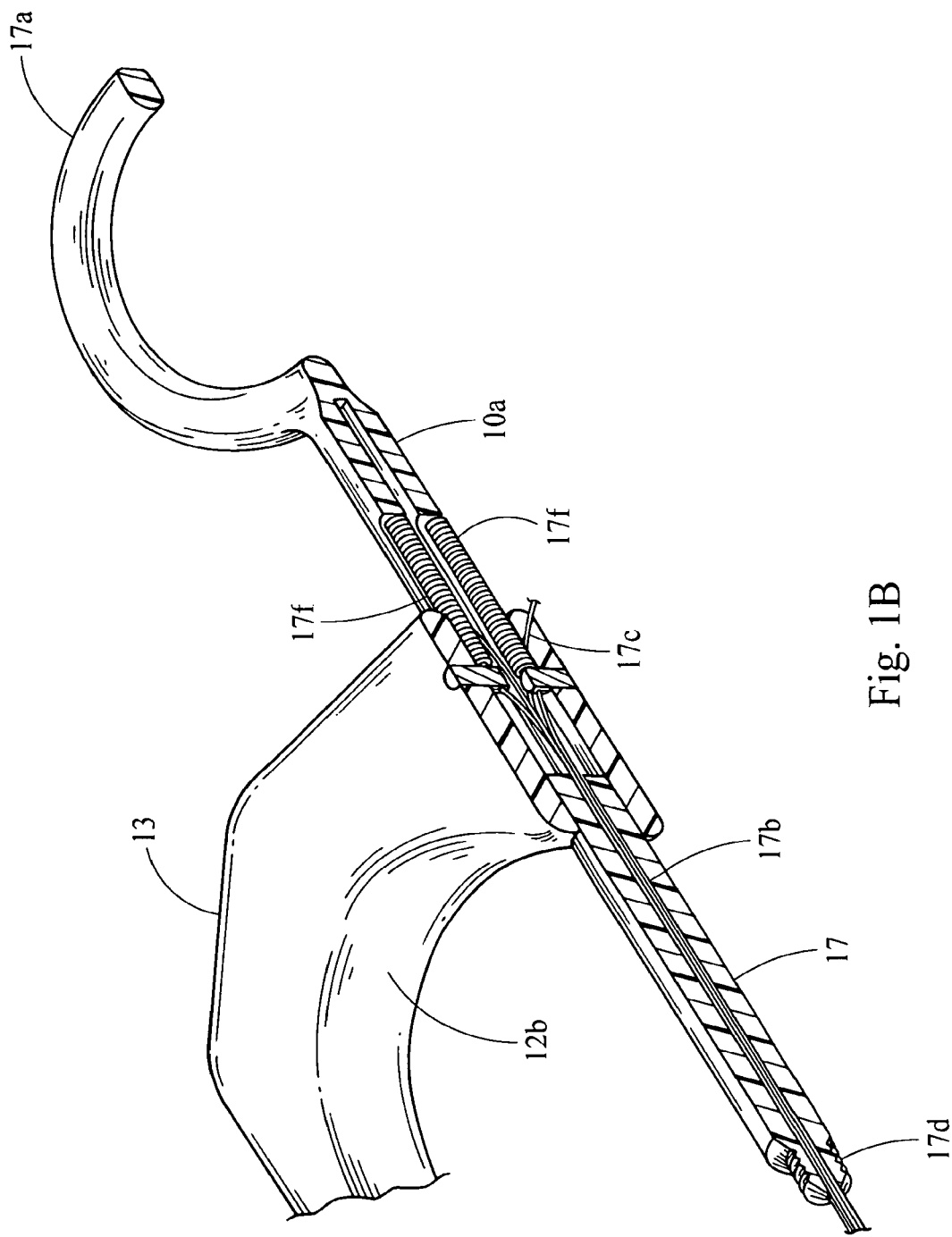
Figure 1D:
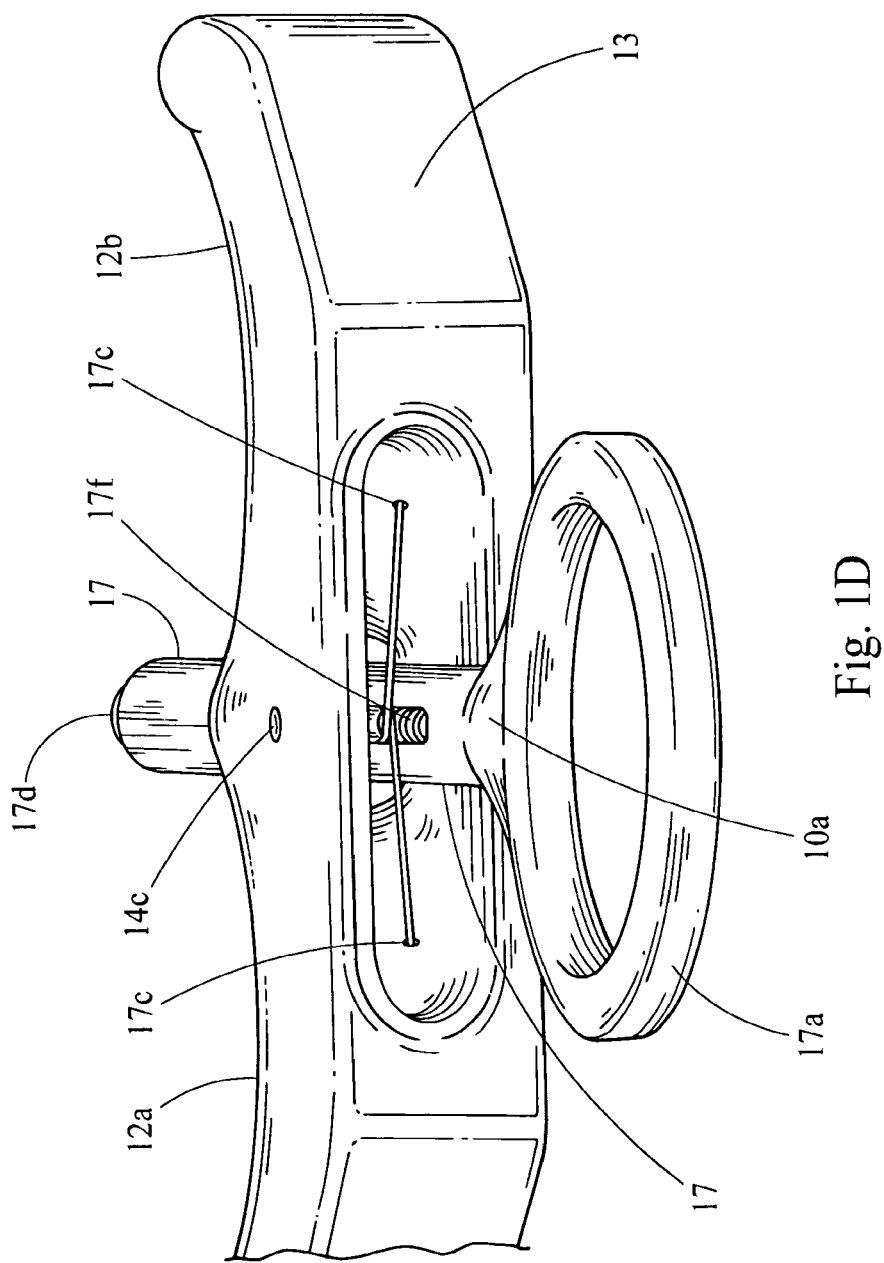
FIG. 1D shows a partial plan view of an embodiment of the device.

FIGS. 1A, 1B, 1C, and 1D depict partial cross-sectional views of an embodiment of the device. Retrieval device 10 has a proximal portion 10a and a distal portion 10b. FIGS. 1B and 1C are cross-sectionals of proximal portion 10a of retrieval device 10 shown in FIG. 1A. FIG. 1C is a perspective view of proximal portion 10a of retrieval device 10 shown in FIG. 1A. Located at distal portion are two grasping wires 11a and 11b that travel through a lumen 15a extending through the sheath 15. Although two grasping wires are depicted, it is contemplated that a greater or lesser amount of grasping wires can be used. Furthermore, it is contemplated that one continuous wire could also be used.

The use of the word "wire" is not intended to be limiting. Throughout the disclosure, grasping wires may be made from stainless steel but are preferably made from a shape memory alloy, including but not limited to Nitinol. Nitinol is available from Memry Corp of Bethel, Conn. and from other suppliers. Grasping wires can also be made from other semi-flexible materials, including but not limited to nylon, plastic, as well as a shape memory polymer. Shape memory polymers are disclosed in U.S. Pat. No. 6,720,402 which is hereby incorporated by reference in its entirety. Grasping wires may also include, but are not limited to, filaments or threads. Grasping wires preferably have a diameter of 0.005-0.009 inches; however, the diameter of grasping wires is not limited to those dimensions. Grasping wires may be larger or smaller depending on the need. Grasping wires are preferably round or flat, however other shapes can be used, such as the near-triangular pre-shaped Delta Wire available from Cook Urological, Spencer, Ind.

At distal portion 10b of retrieval device 10 is a grasping wire connection point 18, which is preferably atraumatic and is used to connect grasping wires 11a, 11b so that they come together in the shape of a basket to keep grasping wires 11a, 11b constrained together. Grasping wires 11a, 11b may be looped together as shown here to form grasping wire connection point 18, but the connection of grasping wires 11a, 11b is not limited to just a loop. Looping of wires is disclosed in U.S. Pat. No. 5,989,266 which is hereby incorporated by reference in its entirety.

Grasping wire restraint disk 16 is located within sheath 15 and can be held in place by ways including but not limited to, gluing, soldering, or sewing into place. Grasping wire restraint disk 16 is used to keep grasping wires 11a, 11b separated once they enter sheath 15. Grasping wire restraint disk 16 can be made from any medically-acceptable material, including but not limited to, polycarbonate, stainless steel, nylon, other metals, and plastics.

Sheath 15 protects grasping wires 11a, 11b from becoming tangled and controls their interaction with the patient. Sheath 15 is preferably made from PVC, but can also be made from materials including, but not limited to, polytetrafluoroethylene (PTFE), polyimide, nylon, polyurethane, polyethylene, or any polymer or semi-flexible metal. Sheath 15 preferably has an outer diameter of 1.5-4.5 Fr., although other sizes can be used and the size should be suitable for insertion through an orifice. The outer diameter of sheath 15 is generally based on the size of the orifice through which it will be introduced.

The articulator 13 houses pivot pins 14a, 14b, and 14c which can be made from many materials, including but not limited to, stainless steel, medically-acceptable polymers, and metals. Articulator 13 can be made from many materials, including but not limited to, rigid nylon, stainless steel, acrylonitrile-butadiene-styrene (ABS) and other medically acceptable polymers and metals. Sheath connection point 17d of body 17 is threaded so that sheath 15 can connect to body 17. Wires 11a, 11b travel through sheath connection point 17d, into body 17, through lumen 17b of body 17, and out through windows 17c into articulator 13. Pivot pin 14c travels through articulator 13 and through body 17. Pivot pin 14c allows articulator 13 to have tilting see-saw movement on either side of transverse axis X-X articulating basket B. Although a basket is depicted, the use of other tools is contemplated including other grasping and sampling devices. Additionally, the wires need not be continuous with the tool, nor do the wires and the tool need to be made from the same material. Pivot pins 14a, 14b, and 14c are configured in a triangle-shape.

First grasping wire 11a is shown pulled through lumen 15a of sheath 15, into sheath connection point 17d, into lumen 17b of body 17, out through windows 17c and around pivot pin 14c where it is attached to pivot pins 14a and 14b. Second grasping wire 11b is attached directly to third pivot pin 14c.

The configuration of pivot pins 14a, 14b, 14c allows the user to articulate basket B from side-to-side, making basket B tilt on its side along transverse axis X-X enabling basket B to grasp an object that may not be directly in-line with basket B. Therefore, articulating basket B allows for basket B to move in a plane in addition outside the longitudinal access.

Furthermore, articulator 13 can move longitudinally along axis Y-Y of body 17 which in turn retracts or extends basket B. Thus, articulator 13 translates relative to body 17; body 17 is stationary with respect to articulator 13 when a thumb (not shown) or other stationary object (not shown) is placed within thumb hole 17a. Two springs 17f sit within body 17 and are in communication with articulator 13 and body 17. Springs are made from stainless steel, although they can be made from any other material so long as they generate an acceptable force to push articulator 13 distally in order to extend basket B. Springs 17f provided resistance against pivot pin 14c which is attached to articulator 13. Thus, when fingers (not shown) apply pressure into either finger groove 12a, 12b and articulator 13 is pulled in the proximal direction, springs 17f are compressed and basket B is retracted. When compression is released from finger groove 12a, 12b, springs 17f are also released and will push articulator 13 in the distal direction, thus extending basket B.

To articulate basket B, the user tilts articulator 13 on either side of transverse axis X-X by pressing a finger (not shown) down into one of the finger grooves 12a, 12b. Tilting articulator 13 in the direction of finger groove 12a will articulate basket B in the direction of finger groove 12a. Similarly, tilting articulator 13 in the direction of finger groove 12b will articulate basket B in the direction of finger groove 12b.

While basket B is being articulated, the user can retract basket B by placing a thumb or finger (not shown) in the thumb-hole 17a and using fingers (not shown) placed in finger grooves 12a, 12b to pull articulator 13 proximally along longitudinal axis Y-Y compressing springs 17f. This moves the entire articulator 13 proximally, and thus, moves pivots pins 14a, 14b, and 14c proximally as well. The proximal movement pulls the respective grasping wires 11a, 11b proximally and retracts basket B. While retracting basket B, the user can articulate basket B by tilting articulator 13 on either side of transverse axis X-X by placing pressure into either finger groove 12a, 12b.

Furthermore, while basket B is being articulated, the user can also extend basket B by releasing the compression on finger grooves 12a, 12b, which releases springs 17f so that they push articulator 13 in the distal direction along longitudinal axis Y-Y. This moves the entire articulator 13 distally, and thus, moves pivots pins 14a, 14b, and 14c distally as well. The distal movement pushes the respective grasping wires 11a, 11b distally and extends basket B. While extending basket B, the user can articulate basket B by tilting articulator 13 on either side of transverse axis X-X by placing pressure into either finger groove 12a, 12b.

Figure 1E:
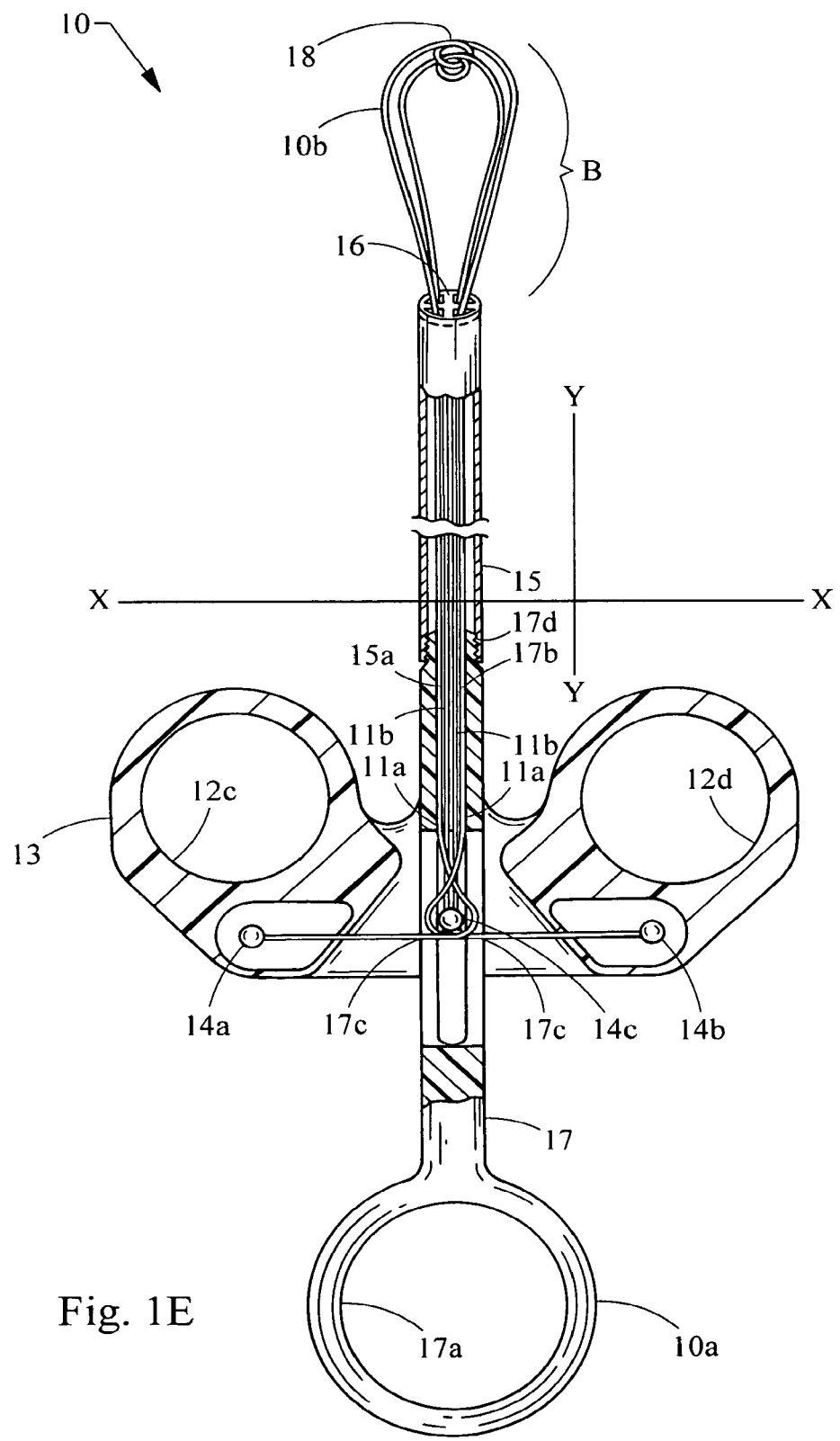
FIG. 1E shows a partial cross-sectional view of an embodiment of the device.

FIG. 1E shows a different embodiment from that shown in FIG. 1A. The embodiment shown in FIG. 1E needs no springs since finger holes 12c, 12d are provided. Thus, when a user places fingers (not shown) within finger holes 12c, 12d, the user is able to move articulator 13 in the distal direction along longitudinal axis Y-Y without the aid of a spring. Further embodiments are shown in FIGS. 2-14D.

Figure 2:
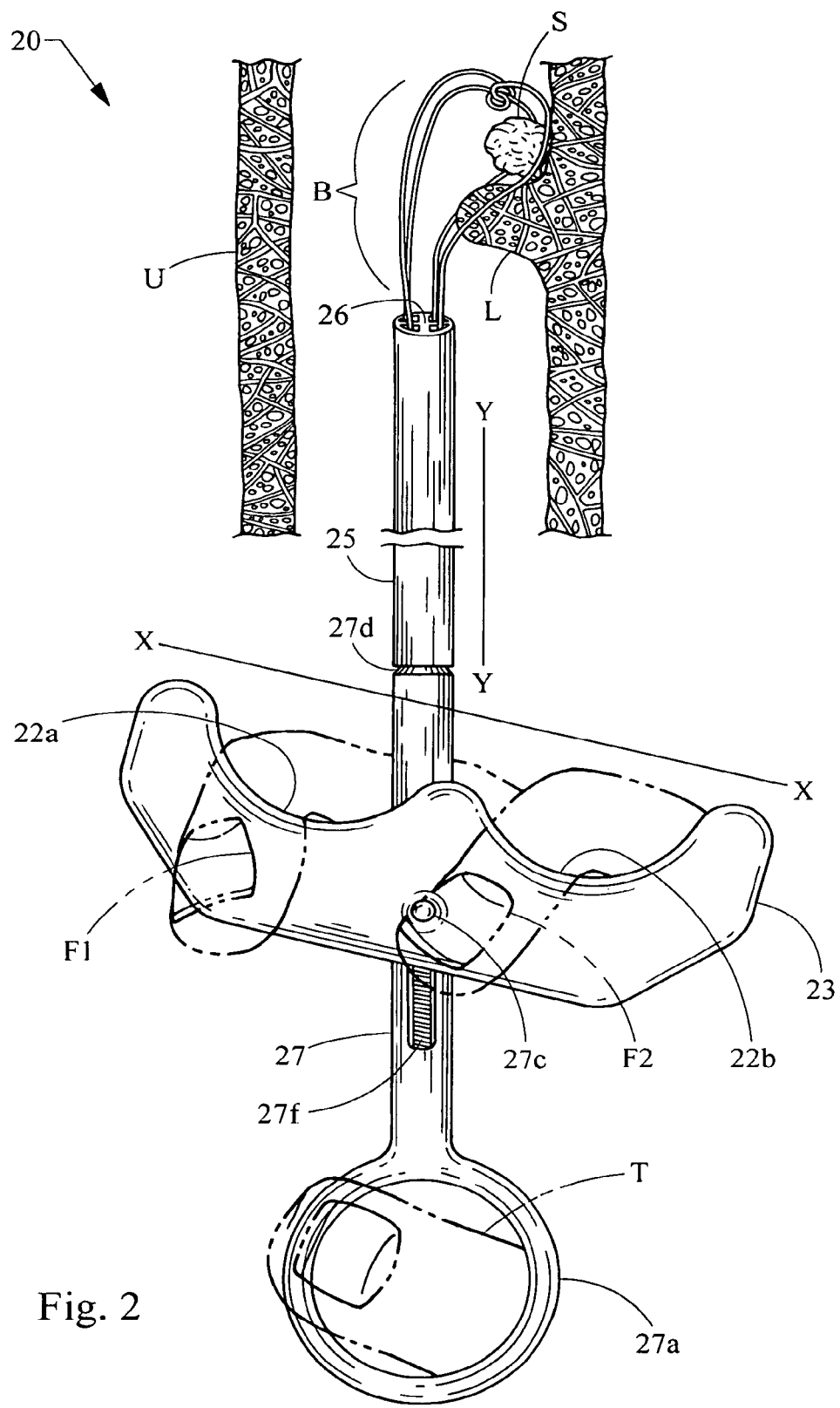
FIG. 2 is an isometric view of the an embodiment of the device.

FIG. 2 is an isometric view of an embodiment of the device. Sheath 25 is connected to body 27 at threaded sheath connection point 27d of retrieval device 20. Basket B enters sheath 25 through grasping wire restraint disk 26. Articulator 23 is shown pushed in the distal direction along longitudinal axis Y-Y and tilted to the right-side of transverse axis X-X. Articulator 23 is moveable along axis Y-Y in the direction of the proximal portion 20a or distal portion 20b of retrieval device 20 when a user pulls or releases articulator 23, which results in springs 27f being compressed or released resulting in basket B being retracted or extended.

Retrieval device 20 is introduced into a ureter U through a functional lumen of an endoscope (not shown), or an access sheath, or other device. After introduction into the patient, retrieval device 20 is advanced to stone S. Here stone S is shown abutted to ledge L of ureter U, and thus, is not directly in front of basket B. When articulator 23 is pulled proximally, springs 27f are compressed and basket B retracts. As articulator 23 is released, springs 27f are released causing articulator 23 to move distally along axis Y-Y, as shown, basket B extends. A first finger F1 is located in a first finger groove 22a, a second finger F2 is located in a second finger groove 22b, and a thumb T is located in thumb hole 27a. While extending basket B, second finger F2 is pressing and tilting articulator 23 so that articulator 23 tilts along axis X-X, via pivot pin 27c. This causes basket B to articulate while simultaneously moving articulator 23 distally along longitudinal axis Y-Y to extend basket B out to stone S to surround stone S. Here, basket B is shown extended and articulated after having just captured stone S.

Figure 3:
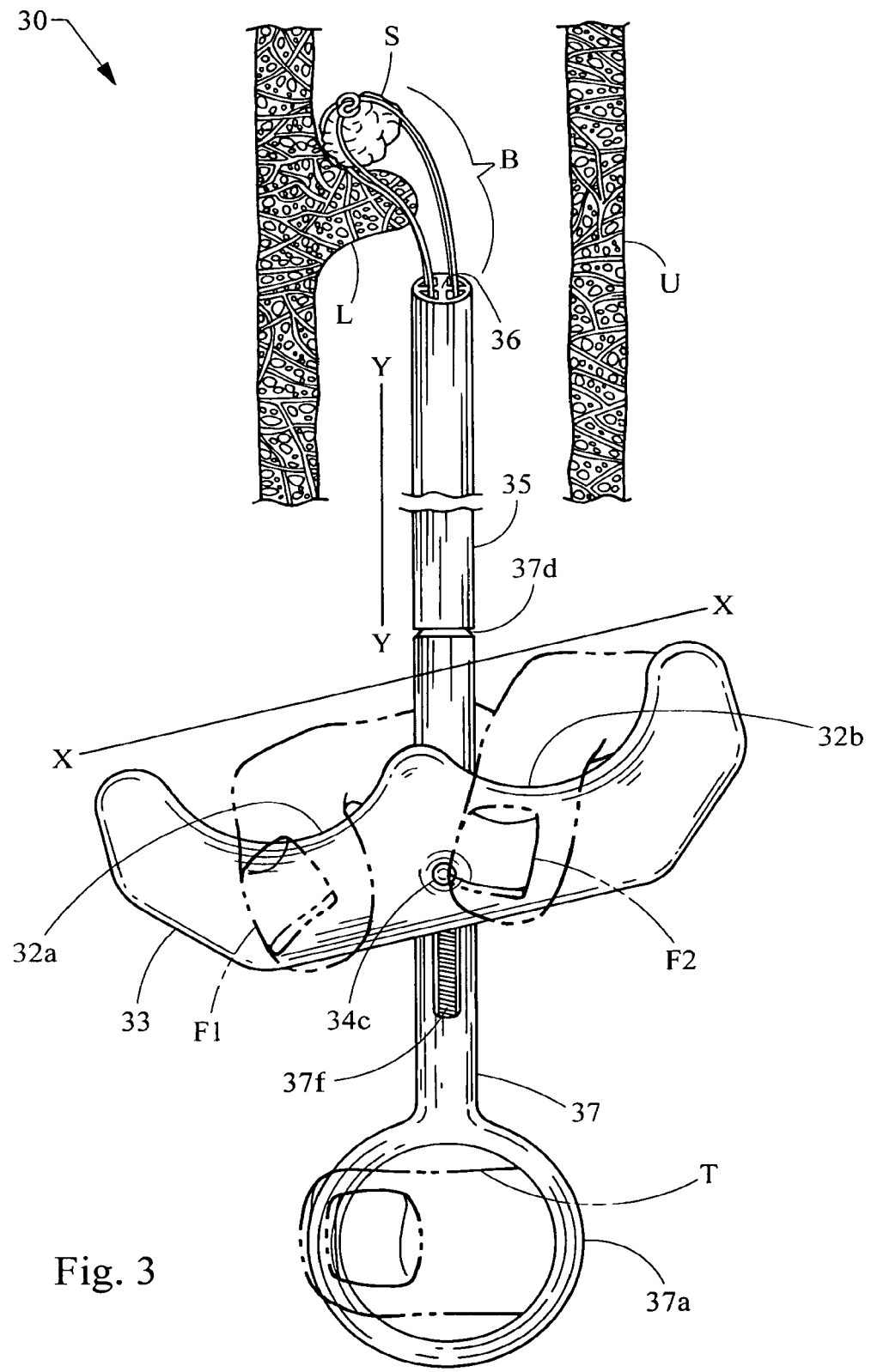
FIG. 3 is an isometric view of an embodiment of the device.

FIG. 3 is an isometric view of another embodiment of the device. Here, the basket B of the retrieval device 30 is shown extended and articulated, having captured a stone S abutting a ledge L within a ureter U. The sheath 35 is connected to body 37 at sheath connection point 37d. Basket B enters sheath 35 through grasping wire restraint disk 36. Articulator 33 surrounds body 37. Articulator 33 has longitudinal movement along longitudinal axis Y-Y. Furthermore, articulator 33 has tilting see-saw movement along either side of transverse axis X-X due to the pivot pin 34c that extends from articulator 33 through body 37. Articulator 33 moves in the direction of the proximal portion 30a and distal portion 30b of the retrieval device 30 when a user pulls and releases, respectively, articulator 33. Thus, body 37 remains stationary with respect to articulator 33 when a thumb T is placed within the thumb-hole 37a. When articulator 33 is released springs 37f are released causing articulator 33 to move in the distal direction (not shown), which causes basket B to extend. As articulator 33 is pulled proximally along axis Y-Y, as shown, springs 37f are compressed and basket B retracts. While retracting basket B, a first finger F1 is located in a first finger groove 32a and a second finger F2 is located in a second finger groove 32b. First finger F1 is pressing and tilting articulator 33 so that articulator 33 tilts along transverse axis X-X causing basket B to articulate. Since basket B is articulated and retracted simultaneously, it can be manipulated in a sweeping motion to capture stone S.

Figure 4A:
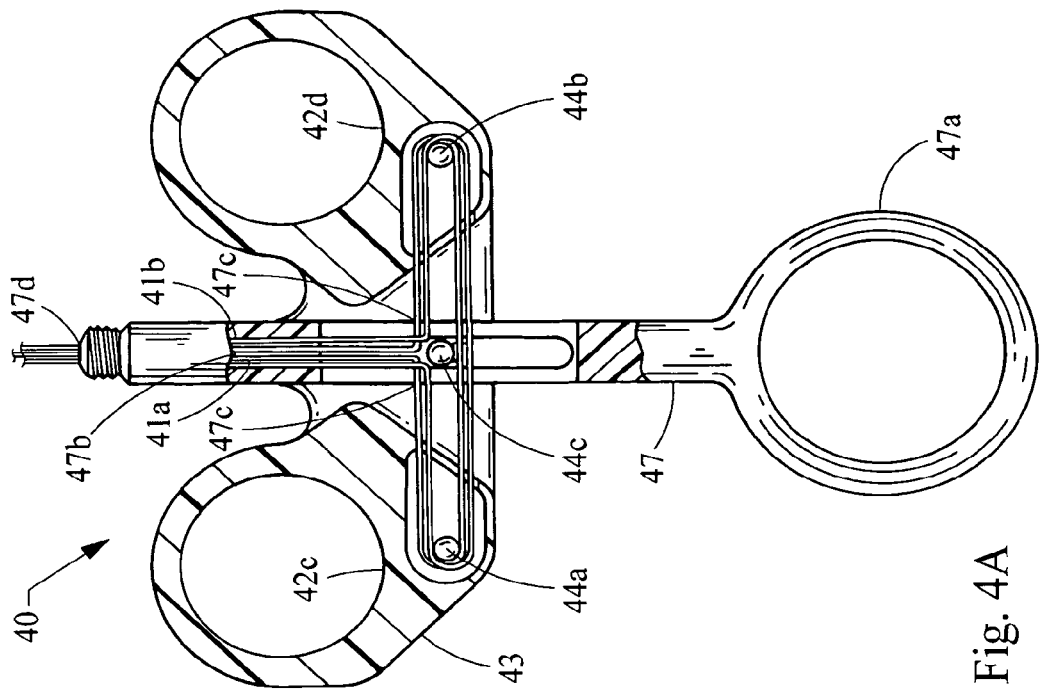
FIGS. 4, and 4A show partial cross-sectional views of the proximal portion of embodiments of the device.
Figure 4:
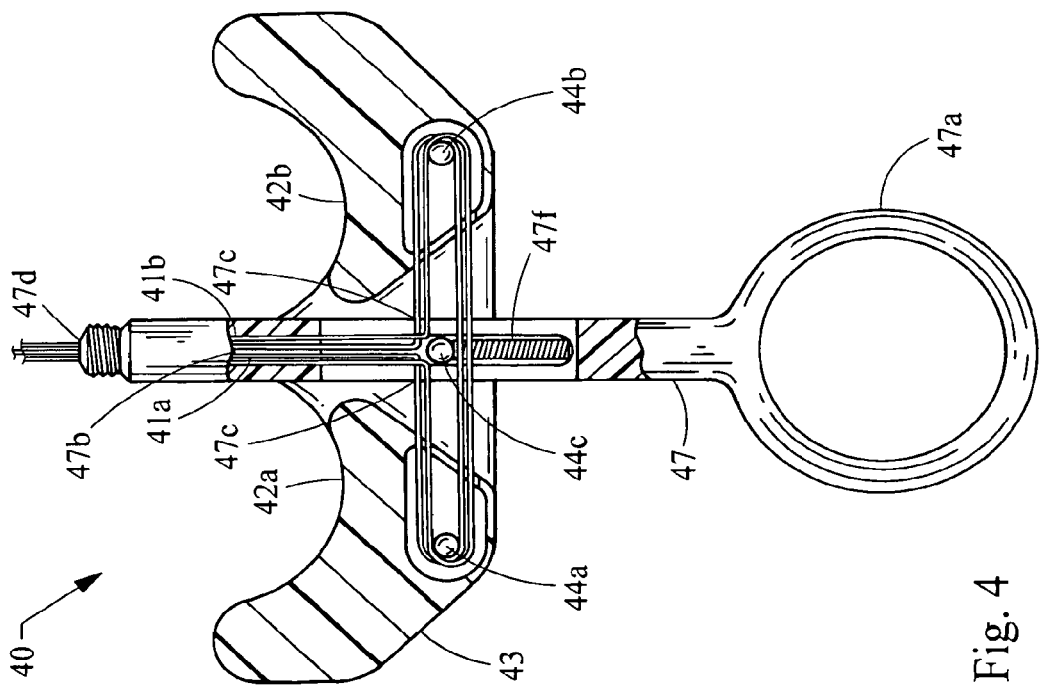

FIGS. 4, 4A, 5, 5A, 5B, 5C, 6, and 6A each show partial cross-sectional views of the proximal portion of embodiments of the device. The figures each show different configurations of the pivot pins housed within the articulator, 43, 53, 63. In FIG. 4 the retrieval device 40 has articulator 43 that houses pivot pins 44a, 44b, 44c. Each grasping wire 41a, 41b enter lumen 47b of body 47 at the sheath connection point 47d. From there, grasping wires 41a, 41b travel through lumen 47b of body 47 and out through windows 47c of body 47 into articulator 43. Each grasping wire 41a, 41b loops around pins 44a, 44b. Pivot pin 44c travels through articulator 43 and into body 47 to allow for tilting see-saw movement of articulator 43 which in turn articulates the basket (not shown). Furthermore, articulator 43 is movably connected to body 47 to allow for longitudinal movement which extends and retracts grasping wires 41a and 41b attached to pivot pins 44a, 44b. Springs 47f are compressed when articulator 43 is pulled in the proximal direction via finger grooves 42a, 42b and thumb hole 47a which retracts the basket (not shown). When springs 47f are released they push articulator 43 in the distal direction which extends the basket (not shown).

FIG. 4A is the same as FIG. 4, except that no springs are needed since articulator 43 has finger loops 42c, 42d that allow a user to push and pull articulator along longitudinal axis of body 47 in order to extend and retract the basket (not shown).

Figure 5A:
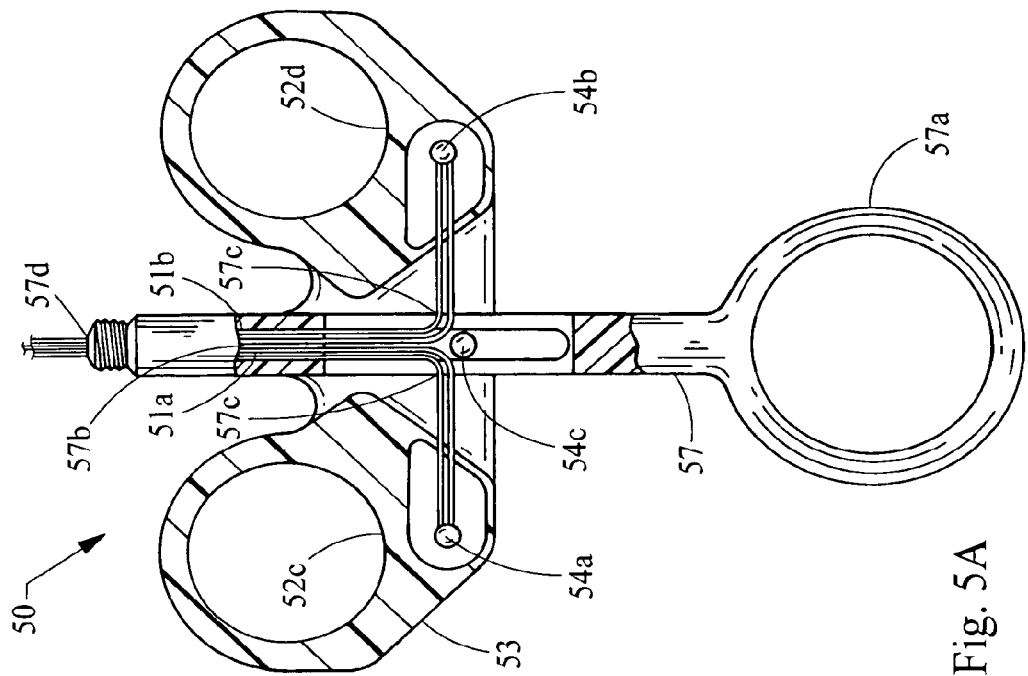
FIGS. 5 and 5A-5C show partial cross-sectional views of the proximal portion of embodiments of the device.
Figure 5:
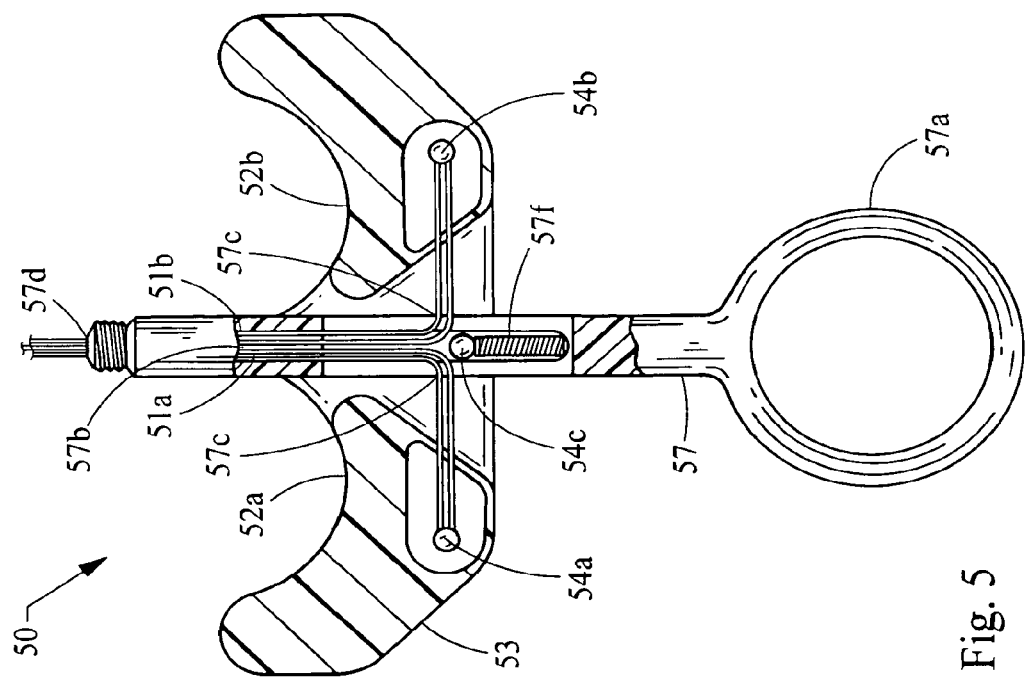

FIG. 5 shows another pivot pin—54a, 54b, 54c—configuration housed within articulator 53 of retrieval device 50. Here, grasping wires 51a, 51b each travel through lumen 57b of body 57 at sheath connection point 57d, out through windows 57c, and into articulator 53. Each end of grasping wires 51a, 51b are each attached to a pivot pin 54a, 54b, located on either side of articulator 53. Pivot pin 54c travels through articulator 53 and into body 57 to allow for tilting see-saw movement which in turn articulates basket (not shown). Furthermore, articulator 53 is movably connected to body 57 to allow for longitudinal movement which extends and retracts grasping wires 51a and 51b attached to pivot pins 54a, 54b. The greater the distance, the less tilting see-saw movement of articulator 53 is required to articulate the basket (not shown). Springs 57f are compressed when articulator 53 is pulled in the proximal direction using finger grooves 52a, 52b, and thumb hole 57a which retracts the basket (not shown). When springs 57f are released they push articulator 53 in the distal direction which extends the basket (not shown).

FIG. 5A is the same as FIG. 5, except that no springs are needed since articulator 53 has finger loops 52c, 52d that allow a user to push and pull articulator along the longitudinal axis of body 57 in order to extend and retract the basket (not shown).

Figure 5C:
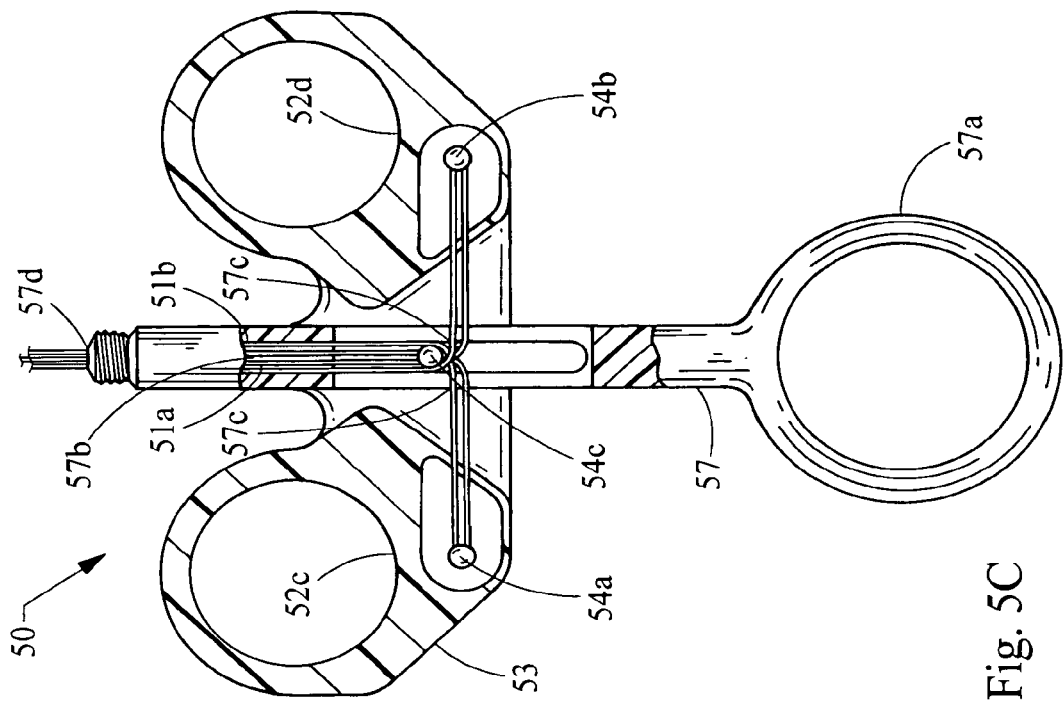
Figure 5B:
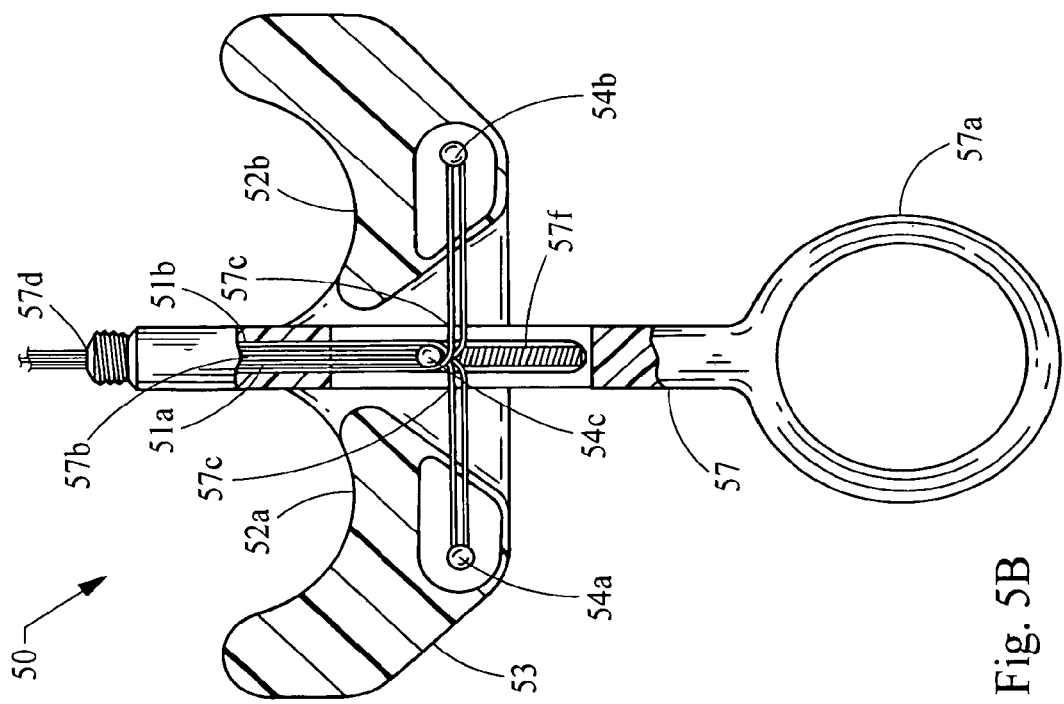

FIG. 5B is the same as FIG. 5 except grasping wires 51*a* and 51*b* are in a different configuration. Here, each grasping wire 51*a*, 51*b* first goes around pin 54*c* before connecting to pivot pins 54*a*, 54*b*.

FIG. 5C is the same as FIG. 5B, except that no springs are needed since articulator 53 has finger loops 52*c*, 52*d* that allow a user to push and pull articulator directly along a longitudinal axis of body 57 in order to extend and retract the basket (not shown).

Figure 6A:
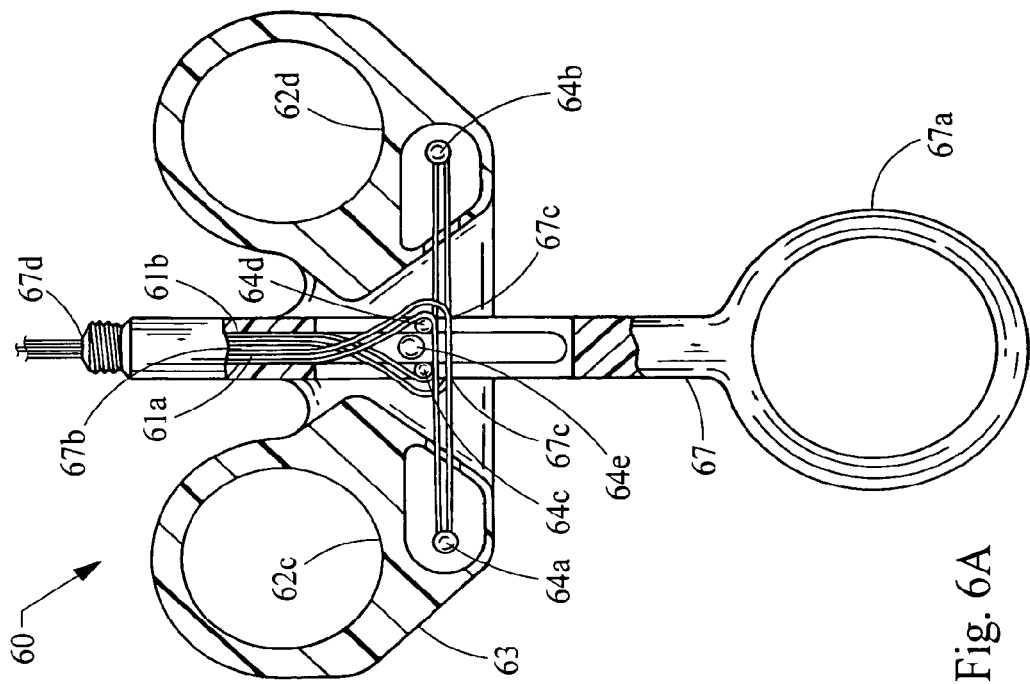
FIGS. 6, and 6A show partial cross-sectional views of the proximal portion of embodiments of the device.
Figure 6:
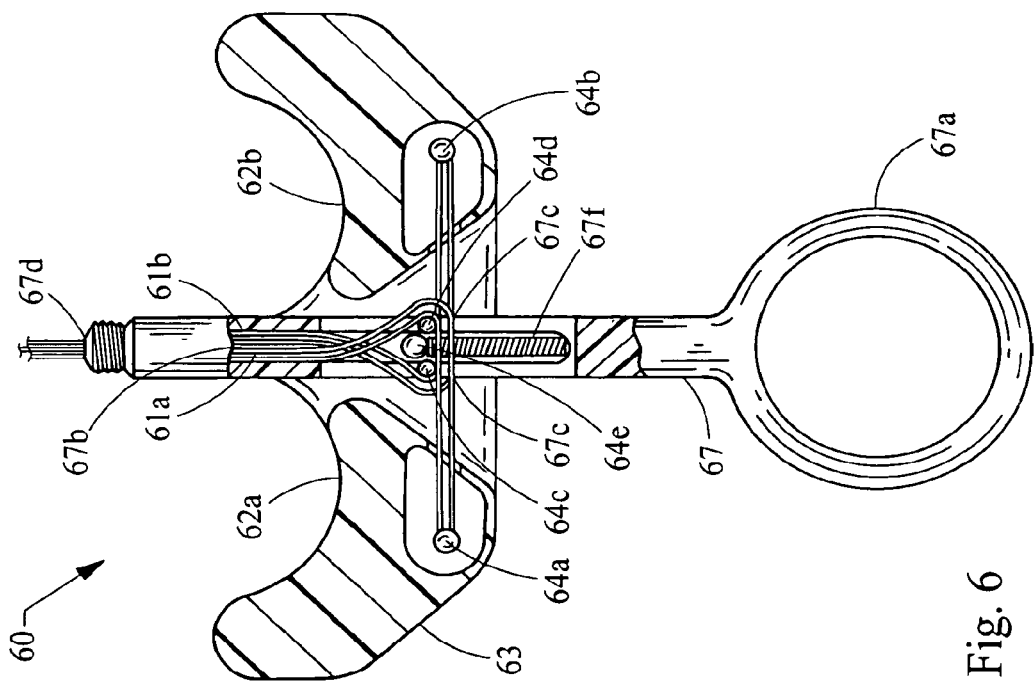

FIG. 6 shows yet another pivot pin configuration—64*a*, 64*b*, 64*c*, 64*d*, 64*e*—housed within articulator 63 of retrieval device 60. Grasping wires 61*a*, and 61*b* enter body 67 at sheath connection point 67*d* and travel through lumen 67*b* of body 67. Grasping wires 61*a* and 61*b* then both loop around fourth pivot pin 64*d*, exit through window 67*c*, and are attached to first pivot pin 64*a*. Grasping wires 61*a* and 61*b* also both loop around third pivot pin 64*c*, exit through window 67*c*, and then are attached to second pivot pin 64*d*. Pivot point 64*e* allows for the articulator 63 to have tilting see-saw movement to allow the basket (not shown) to be articulated. Articulator 63 to move longitudinally proximally and distally along longitudinal axis of body 67. This configuration allows for both pushing and pulling of the basket (not shown). Springs 67*f* are compressed when articulator 63 is pulled in the proximal direction using finger grooves 62*a*, 62*b*, and thumb hold 67*a* which retracts the basket (not shown). When springs 67*f* are released they push articulator 63 in the distal direction which extends the basket (not shown).

FIG. 6A is the same as FIG. 6, except that no springs are needed since articulator 63 has finger loops 62*c*, 62*d* that allow a user to push and pull articulator along longitudinal axis of body 67 in order to extend and retract the basket (not shown).

Figure 7A:
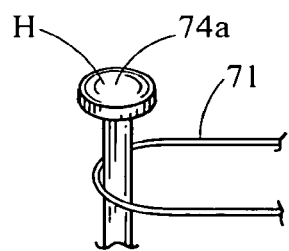
FIGS. 7A-7E are isometric views of pivot pins of embodiments of the device.

FIGS. 7A-7E are isometric views of pivot pins of embodiments of the device. In FIG. 7A, pivot pin 74*a* is a nail-shaped pin having a head H that has a greater diameter than the body. This prevents grasping wire 71 from slipping off of pivot pin 74*a* when the basket (not shown) is articulated, extended, and/or retracted.

Figure 7B:
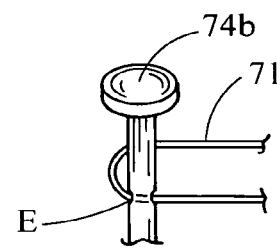

FIG. 7B shows an alternate embodiment of pivot pin 74*b* having an eye E in which grasping wire 71 is threaded through to prevent it from becoming detached from pivot pin 74*b* when the basket (not shown) is articulated, extended, and/or retracted.

Figure 7C:
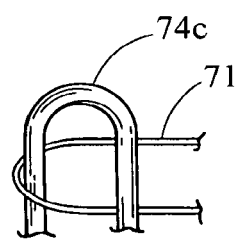

FIG. 7C shows a pivot pin 74*c* with an arch shape through which grasping wire 71 is threaded to prevent grasping wire 71 from becoming detached from pivot pin 74*c* when the basket (not shown) is articulated, extended, and/or retracted.

Figure 7D:
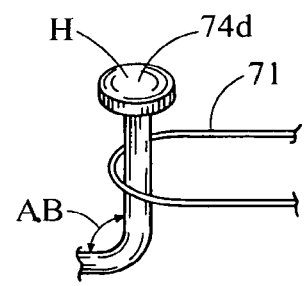

FIG. 7D shows a pivot pin 74*d* having a "j" shape, an angular bend AB, and a head H that has a larger diameter than the body. Pivot pin 74*d* keeps grasping wire 71 in place when the basket (not shown) is articulated, extended, and/or retracted.

Figure 7E:
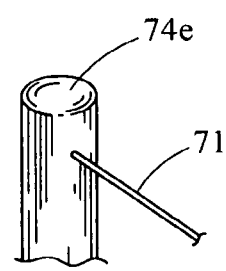

FIG. 7E shows a pivot pin 74*e* with grasping wire 71 attached to pivot pin 74*e* by way of soldering.

FIGS. 8A and 8B are isometric views of the proximal portion of embodiments of the device. In FIG. 8A the articulator 83 of retrieval device 80 has ergonomically-shaped finger grooves 82*a*, 82*b* and thumb-hole 87*a*. The shape provides a comfortable fit for fingers F1, F2 and thumb T. Grasping wires 81*a*, 81*b* enter body 87 at sheath connection point 87*d*, travel though lumen 87*b*, and connect to pivot pins (now shown). Pivot pin 87*c* allows articulator 83 to have tilting see-saw movement in order to allow for the basket (not shown) to articulate. Basket (not shown) retraction occurs by moving articulator 83 proximally along longitudinal axis of body 87 which compresses springs 87*f*. Basket (not shown) extension occurs by releasing articulator 83 which decompresses springs 87*f* causing articulator 83 to move along body 87.

FIG. 8B shows an alternate configuration of articulator 83 of retrieval device 80. Here, articulator 83 has ergonomically-shaped finger holes 82*c*, 82*d* for fingers F1, F2. No springs are needed in this embodiment since finger holes 82*c*, 83*d* allow the user to pull and push articulator 83 directly thus enabling basket (now shown) retraction and extension.

Figure 9A:
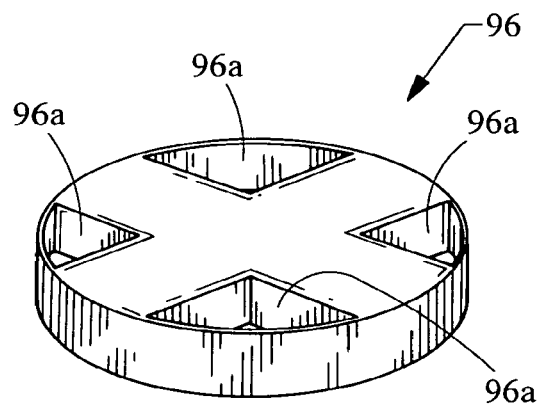
FIGS. 9A-9C are isometric views of grasping wire restraint disks of embodiments of the device.
Figure 9B:
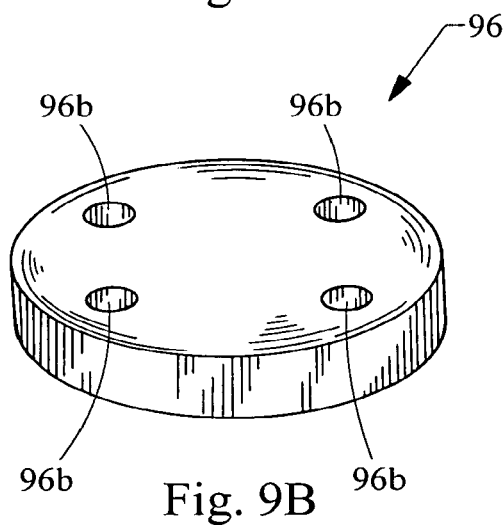
Figure 9C:
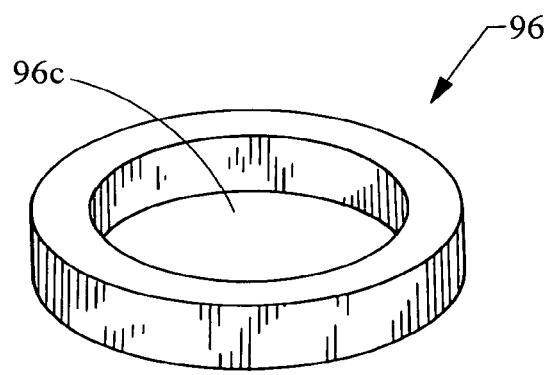

FIGS. 9A-9C are isometric views of grasping wire restraint disks. In FIG. 9A the grasping wire restraint disk 96 is shown having four guide holes 96*a* for wires in the shape of a cross. Each grasping wire (not shown) is threaded through a single lumen 96*a* of grasping wire restraint disk 96.

FIG. 9B shows a grasping wire restraint disk 96 wherein four lumens are created with circular-shaped openings 96*b* cut into grasping wire restraint disk 96 creating four guide holes. Each of grasping wires (not shown) are threaded through a single lumen 96*b* of grasping wire restraint disk 96.

FIG. 9*c* shows a grasping wire restraint disk 96 wherein grasping wires (not shown) are treaded through a single lumen 96*c*.

Figure 10A:
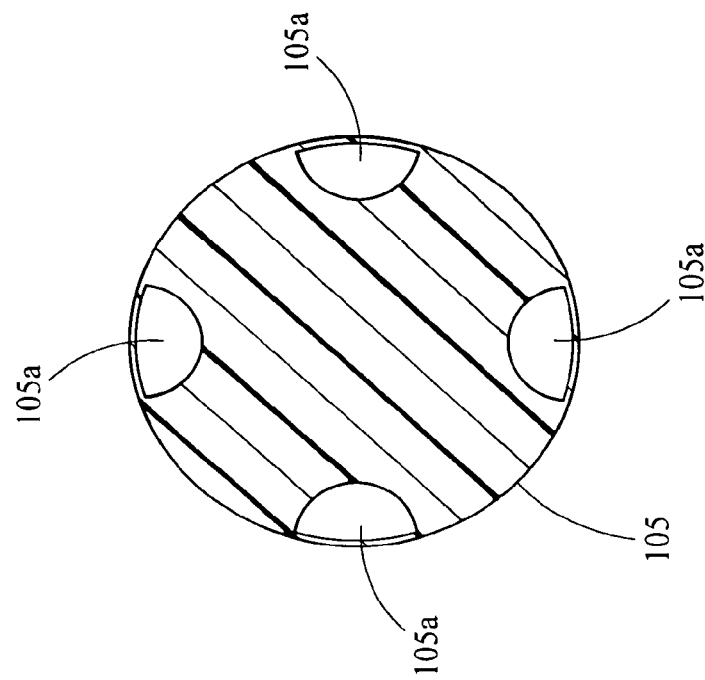
FIG. 10A is a cross-sectional view of FIG. 10 at line 10A.
Figure 10:
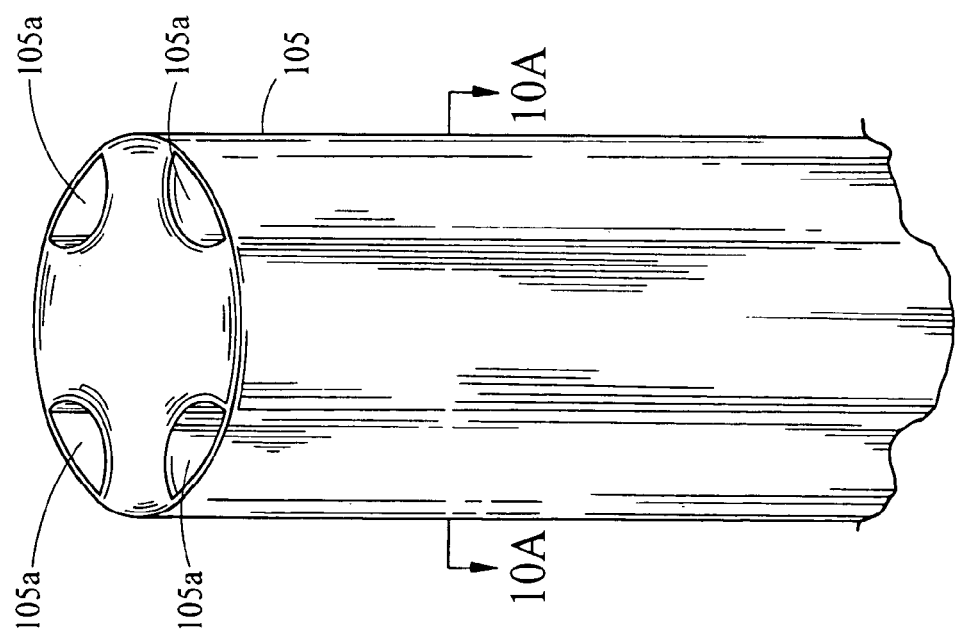
FIG. 10 is an isometric view of a sheath of an embodiment of the device.
Figure 10C:
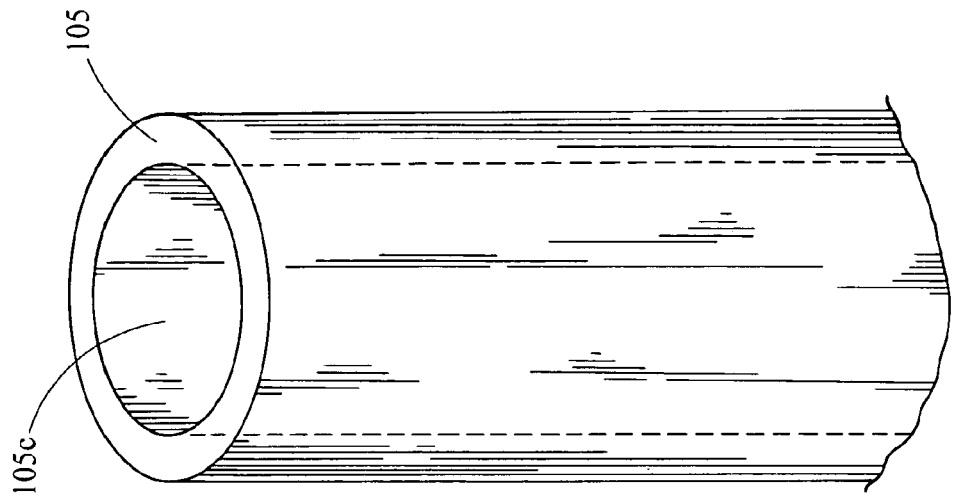
FIG. 10B-10C are isometric views of a sheath of embodiments of the device.
Figure 10B:
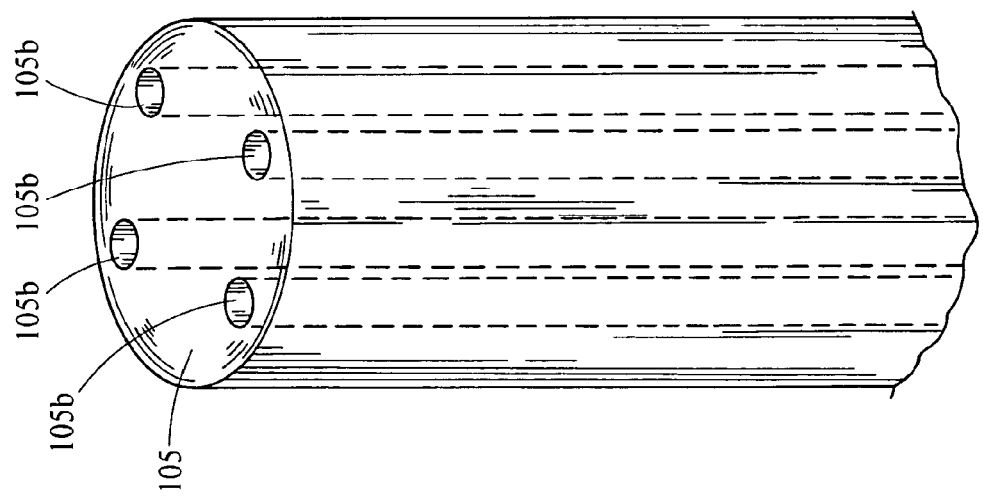

FIG. 10 is an isometric view of an optional sheath for the retrieval device. Here, instead of maintaining grasping wire (not shown) separation by using a grasping wire restraint disk (not shown) the sheath 105 itself has four semi-circular lumens 105*a*. A cross section of sheath 105 at line-10A is depicted in FIG. 10A. Each grasping wire (not shown) are threaded through a lumen 105*a* of sheath 105 so that the grasping wires (not shown) do not become tangled and stay separated as they travel through sheath 105. FIG. 10B depicts an alternate configuration of circular-grasping wire lumens 105*b* built into sheath 105. FIG. 10C depicts an alternate configuration of a single circular grasping wire lumen 105*c* built into sheath 105.

Figure 11:
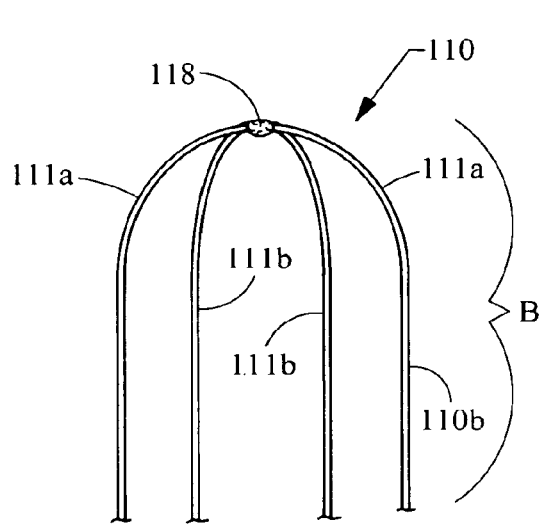
FIG. 11 is a close-up view of the distal portion of an embodiment of the device.

FIG. 11 is a close-up view of the distal portion 110*b* of an embodiment of retrieval device 110. Here, grasping wires 111*a*, 111*b* are connected at grasping wire connection point 118 via a soldered point in order to form the top of basket B.

Figure 12:
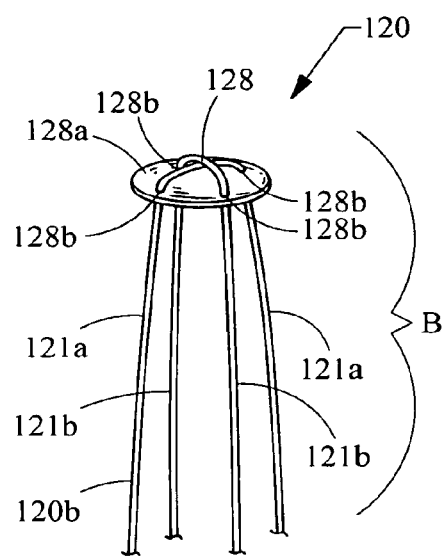
FIG. 12 is a close-up view of the distal portion of an embodiment of the device.

FIG. 12 is a view of the distal portion 120*b* of retrieval device 120. Here, grasping wires 121*a*, 121*b*, are connected at grasping wire connection point 128 via a grasping wire connection disk 128*a* in order to form the top of basket B. Grasping wire connection disk 128*a* can be made from many materials including polycarbonates, stainless steel, nylon, and polymers. Grasping wire connection disk 128*a* contains four holes 128*b* through which grasping wires 121*a*, 121*b* are threaded.

Figure 13:
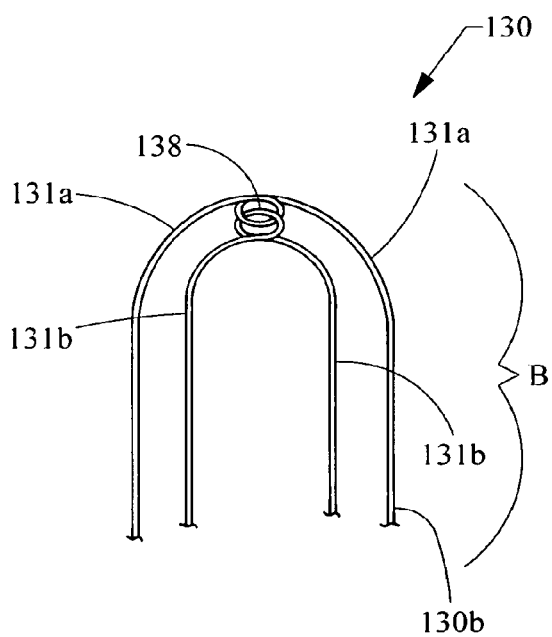
FIG. 13 is a close-up view of the distal portion of an embodiment of the device.

FIG. 13 is a view of the distal portion 130*b* of retrieval device 130. Here, grasping wires 131*a*, 131*b* are connected at grasping wire connection point 138 via a loop-in-loop configuration in order to form the top of basket B.

Figure 14A:
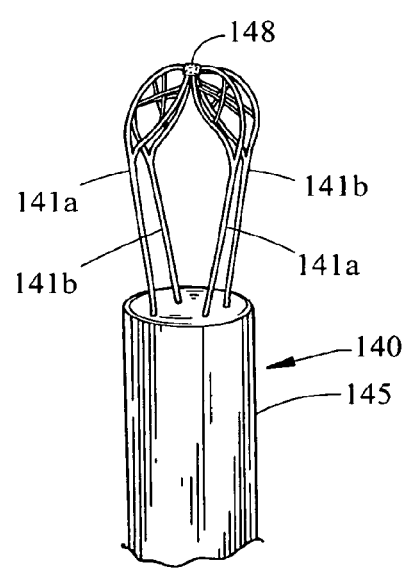
FIG. 14A is a perspective view of the distal portion of an embodiment of the device.

FIG. 14A is a perspective view of the distal portion of retrieval device 140. Each grasping wire 141*a*, 141*b* is connected at a soldered grasping wire connection point 148 and then threaded into sheath 145. The net configuration of grasping wires 141*a*, 141*b* may enable better retrieval of smaller stones or calculi that could slip between the wires if there were no net.

Figure 14B:
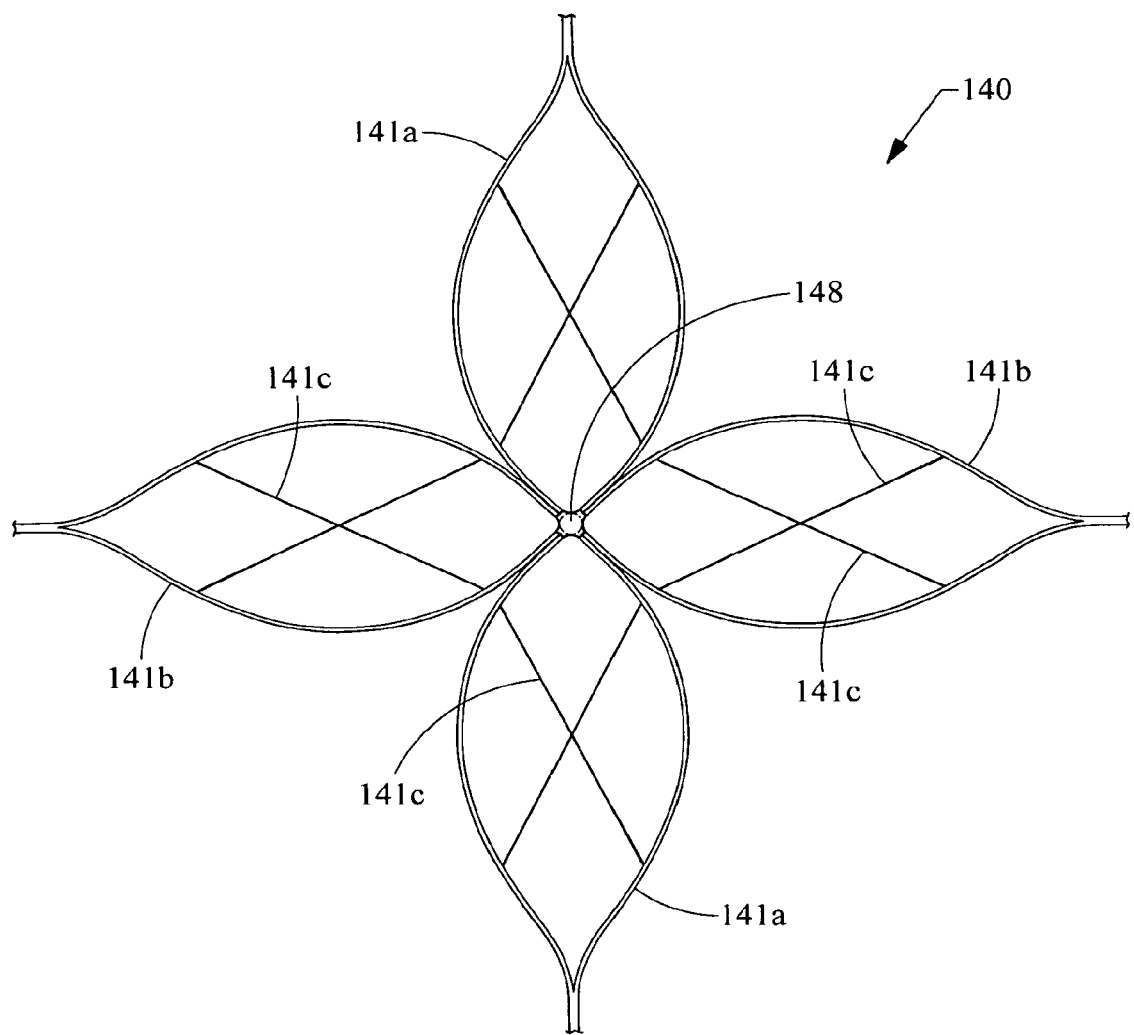
FIGS. 14B-14D are frontal views of the distal portion of embodiments of the device.
Figure 14C:
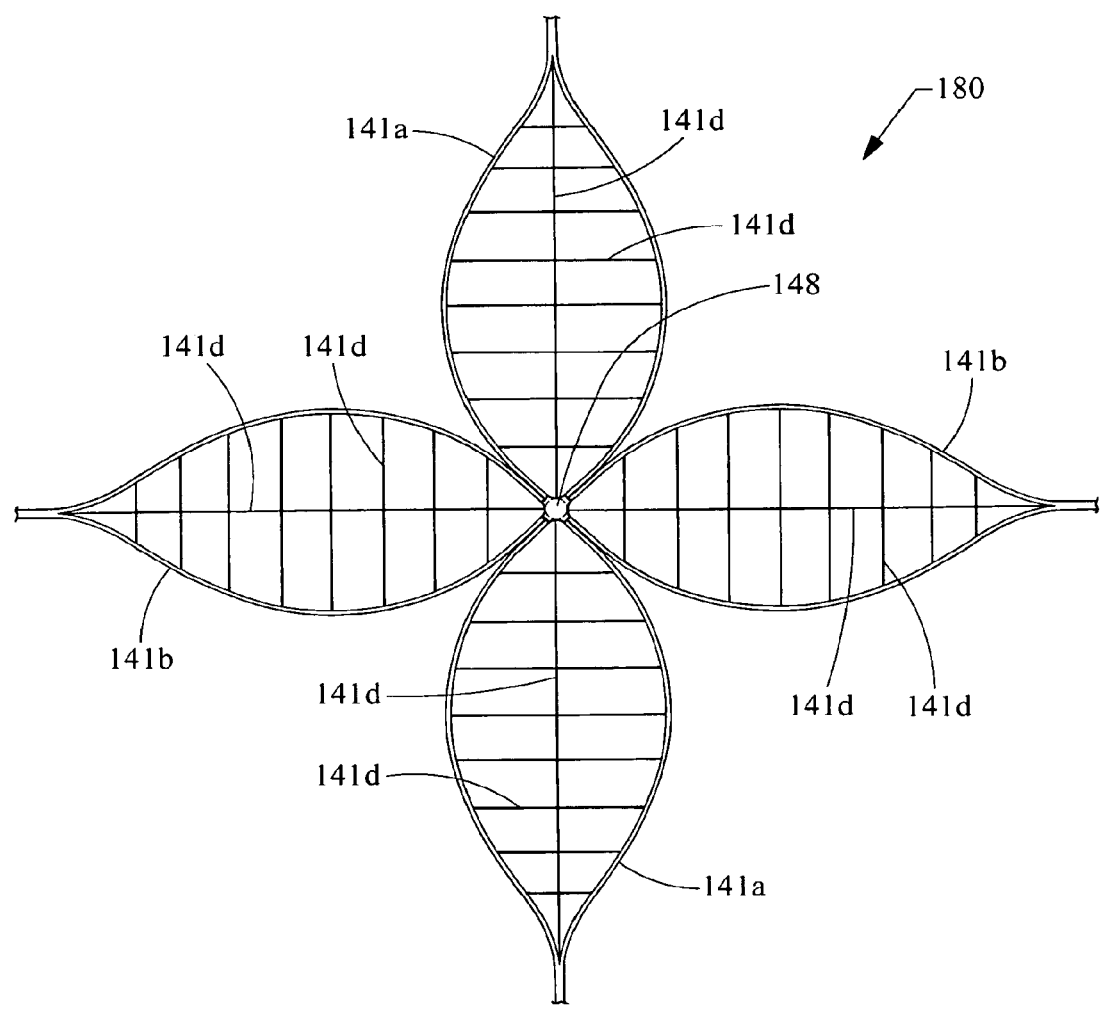
Figure 14D:
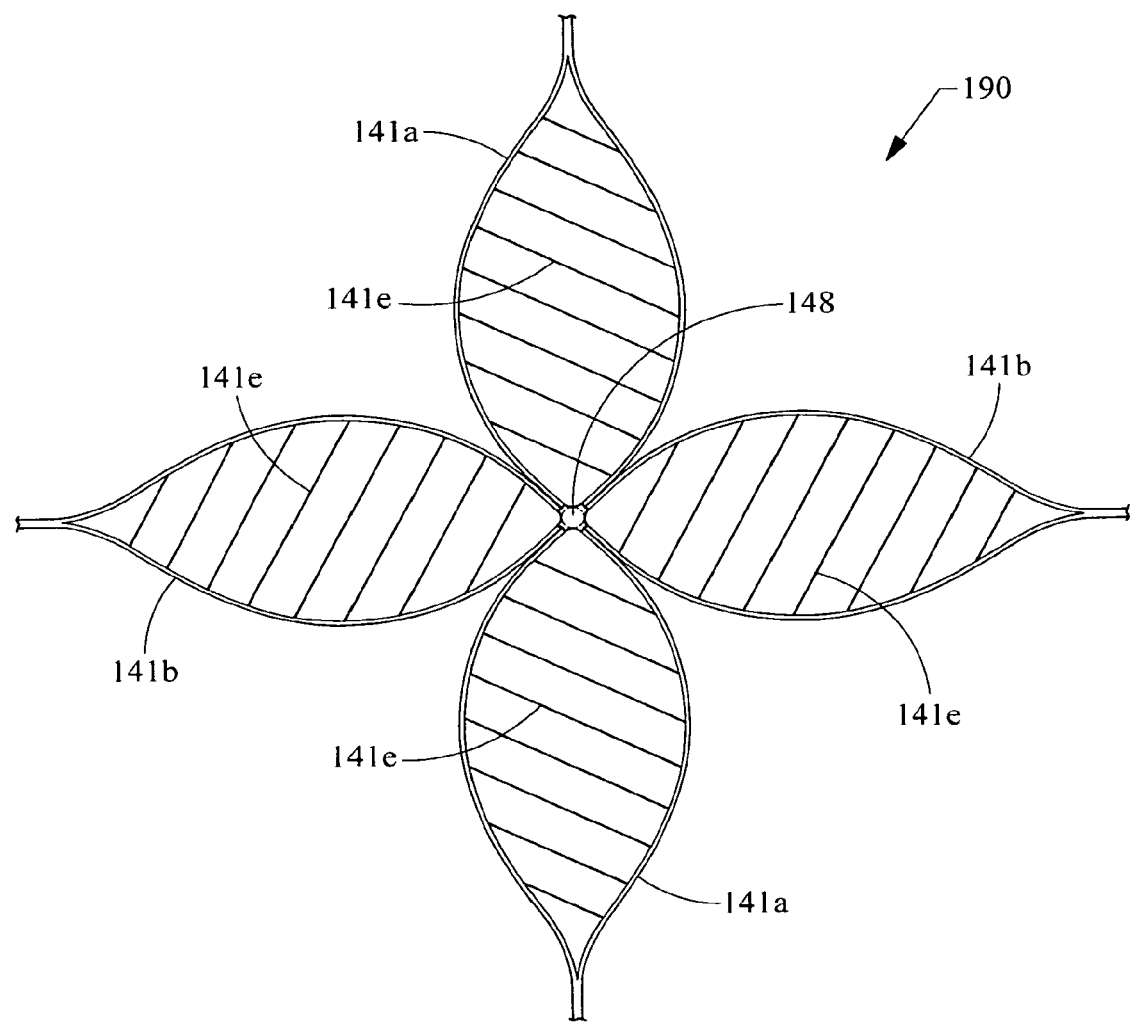

FIGS. 14B-14D are frontal views of retrieval device embodiments 140, 180, 190. Each show grasping wire 141*a*, 141*b* connected at a soldered grasping wire connection point 148. Each figure depicts a different net-configuration of wire fibers 141c, 141d, 141e. Wire fiber 141c, 141d, 141e configurations are not limited to those depicted. Depending on the shape of the object to be retrieved, different wire fiber 141c, 141d, 141e configurations may result in a better retrieval success rate of smaller stones (not shown), calculi (not shown), or other objects (not shown).

Figure 15:
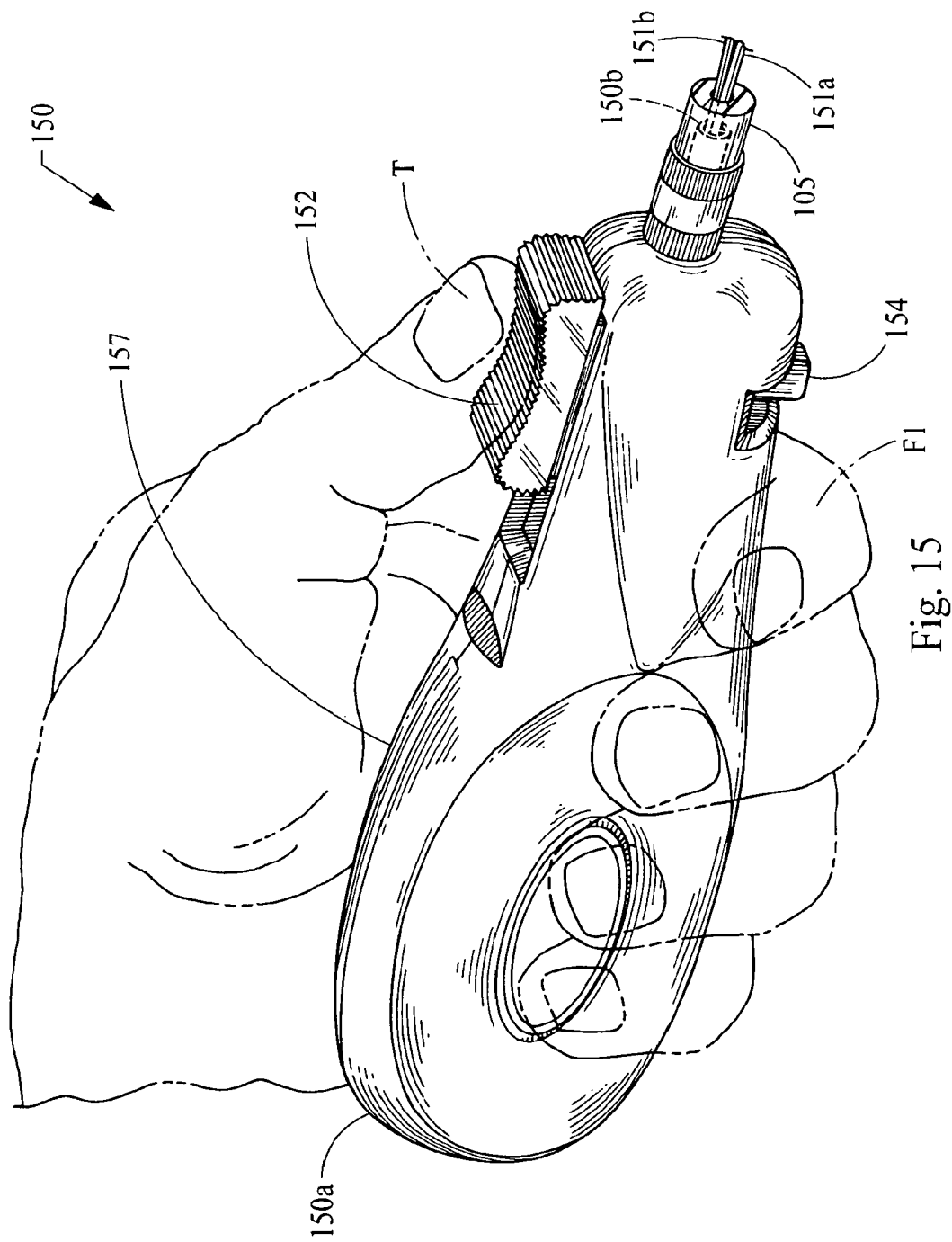
FIGS. 15-18 depict another embodiment of the device.
Figure 16:
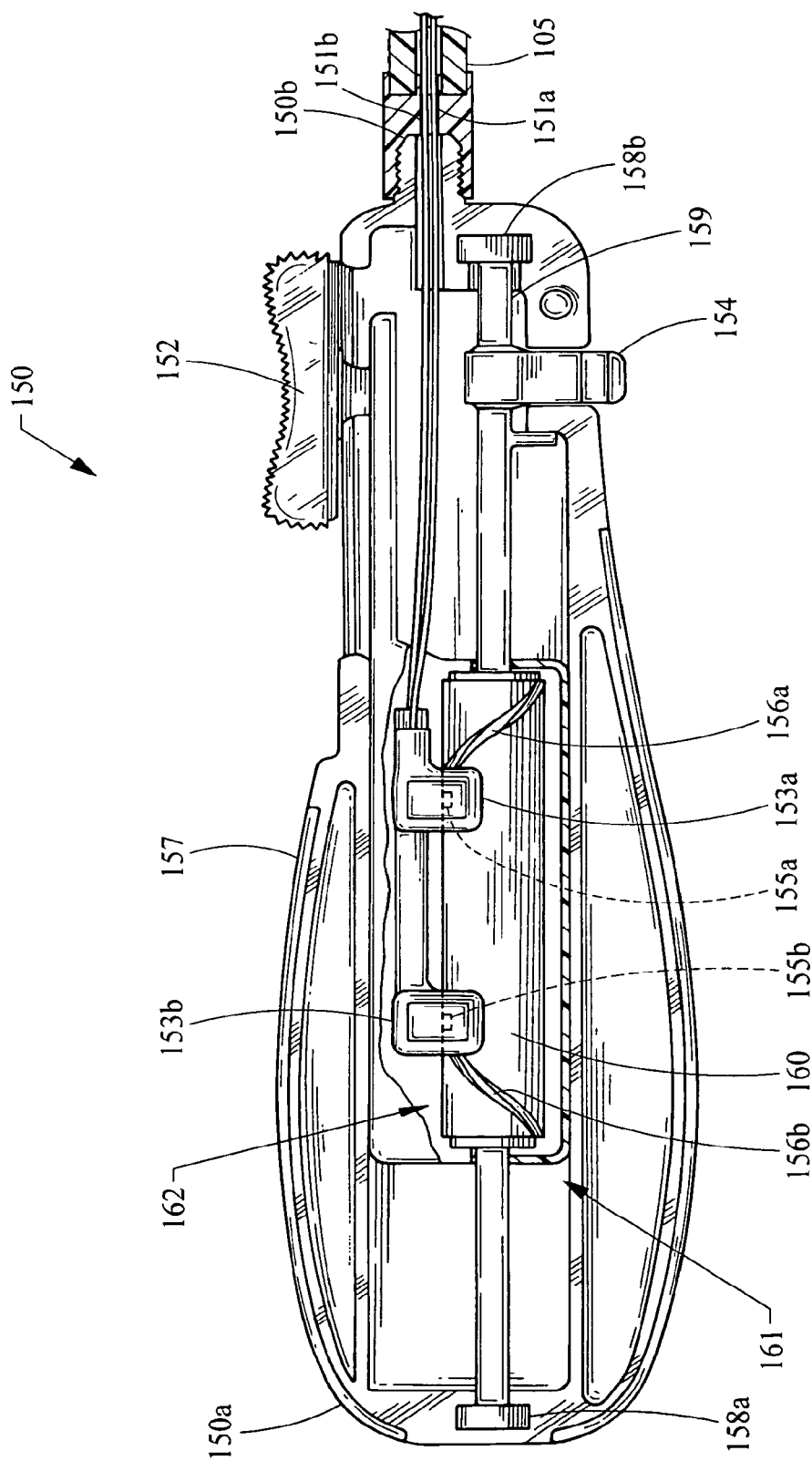
Figure 17:
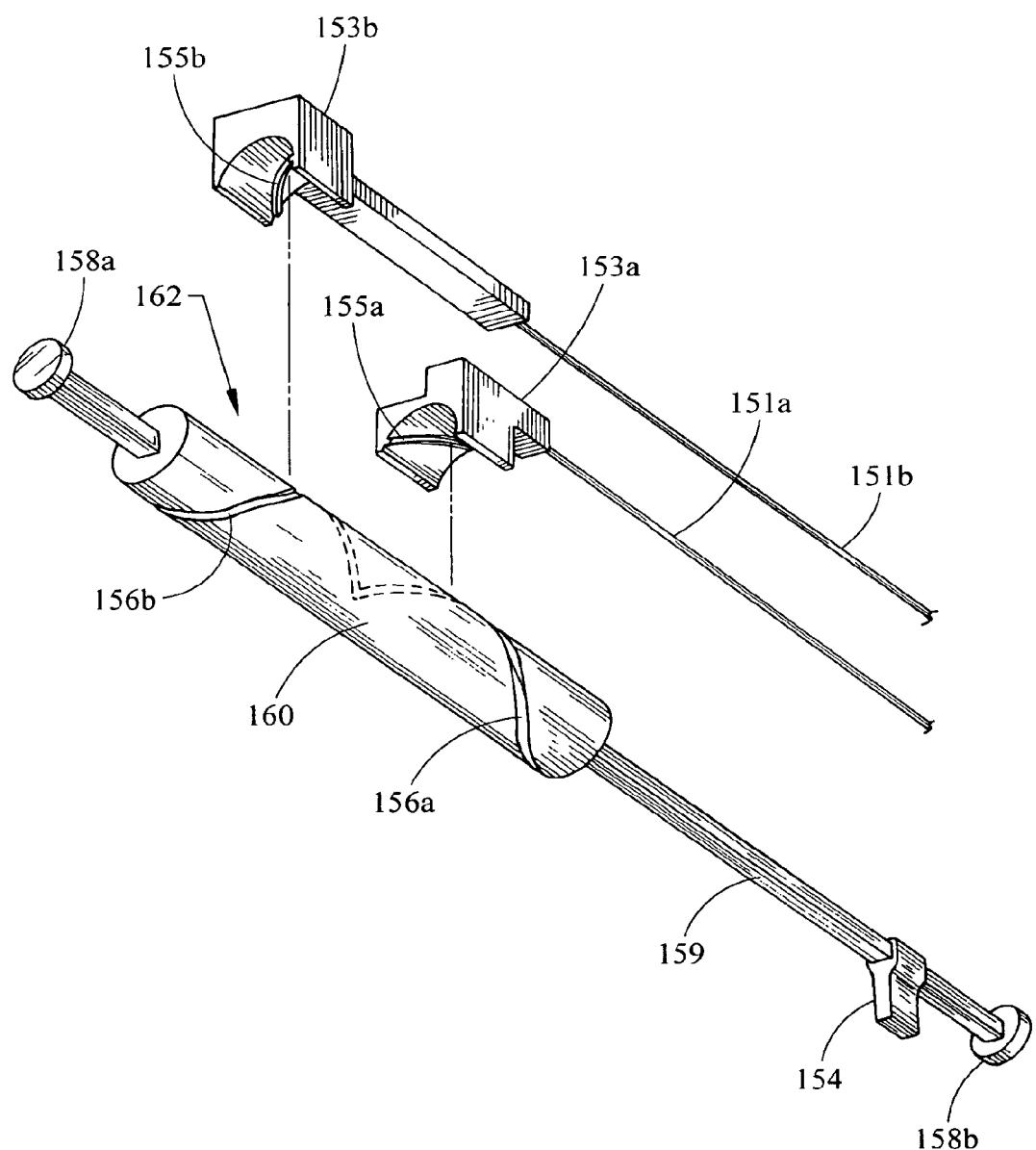

FIGS. 15-17 depict different views of another embodiment of the device. FIG. 15 is a side-view of a retrieval device 150 having a proximal portion 150a and a distal portion 150b. FIG. 16 is a partial cross-sectional view of retrieval device 150. FIG. 17 is an exploded view of articulator 162.

Body 157, and the components housed therein including an articulator 162 and a slide assembly 161 depicted in FIGS. 16-17, can be made from many materials, including but not limited to, rigid nylon, stainless steel, acrylonitrile-butadiene-styrene (ABS) and other medically acceptable polymers and metals. Body 157 is preferably a snap-fit housing consisting of two pieces that house that components depicted in FIGS. 16-17.

Figure 18:
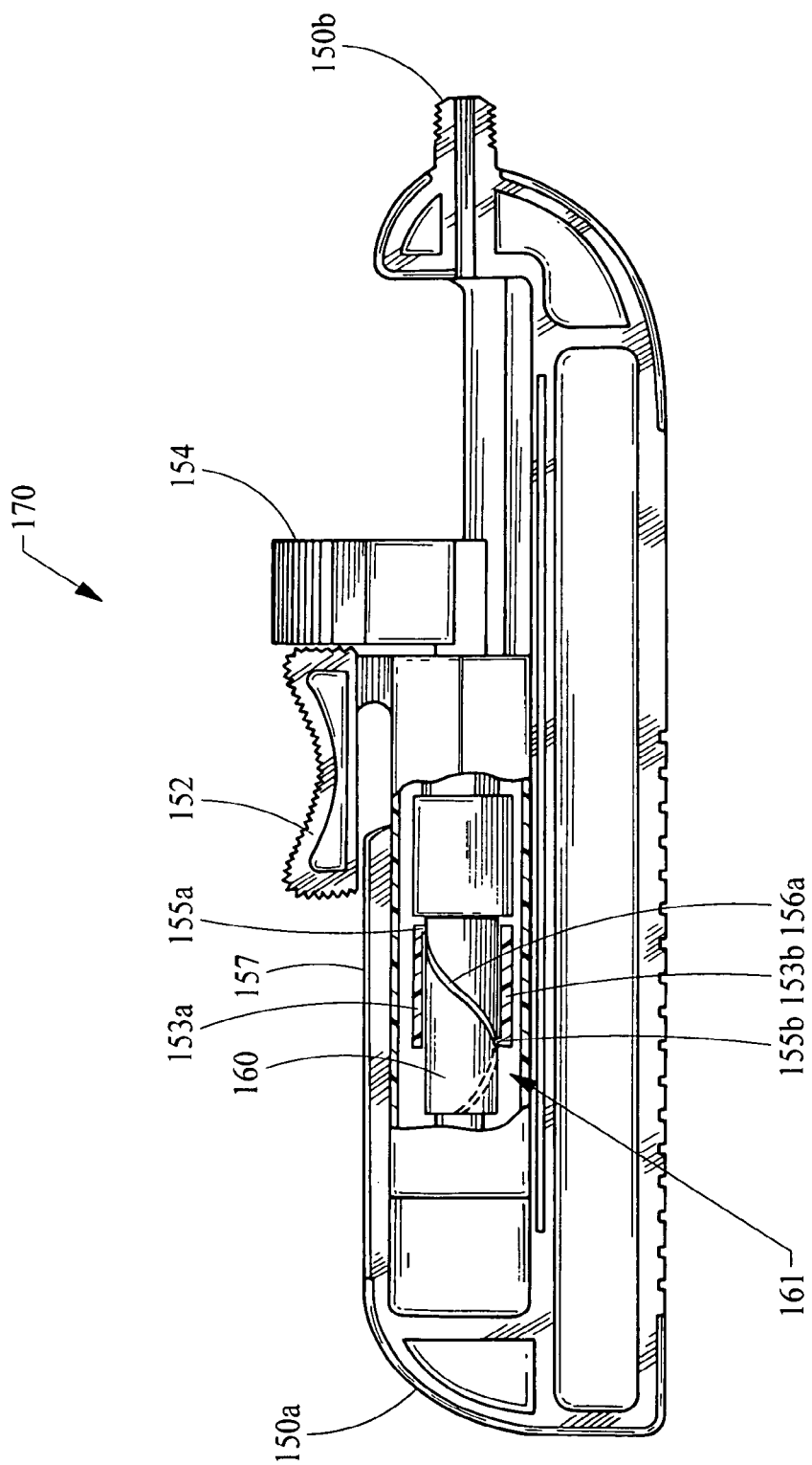

Distal portion of grasping wires come together to form a basket (not shown). Each of grasping wires 151a and 151b is disposed through optional sheath 105 and is connected to a wire pivot 153a, 153b respectively. Wire pivots 153a, 153b each have a male thread 155a, 155b, respectively, that engages with female thread 156a, 156b, respectively, located on articulator drum 160. Articulator drum 160 has a post 159 disposed therethrough. Articulator drum 160 is rotateably attached to slide assembly 161 which is slideably attached to body 157 and is held in place by each of anchors 158a, 158b that are fixedly attached to post 159 and rotateably attached to body 157. Tilting lever 154 from side to side causes post 159 and articulator drum 160 to rotate in the direction that lever 154 is pushed. Rotation of the drum 160 is not limited to use of lever 154; the device can also be driven by a gear set, a wheel, or any device capable of causing rotation. As articulator drum 160 is rotated, wire pivots 153a, 153b move opposite each other in the proximal 150a or distal 150b direction causing each of wires 151a, 151b to move in the direction that wire pivots 153a, 153b move; accordingly, this movement causes the basket to articulate from side to side. Pulling slide 152 in the proximal direction 150a causes the basket to retract because articulator drum 160 and its component wire pivots 153a, 153b and grasping wires 151a, 151b are moved in the proximal direction. Pushing slide 152 in the distal direction 150b causes the basket to extend because articulator drum 160 and its component wire pivots 153a, 153b and grasping wires 151a, 151b are moved in the distal direction. In addition, the basket can be articulated by tilting lever 154 with finger F1 and simultaneously retracted or extended by moving slide 152 in the proximal 150a or distal 150b direction with thumb T. The embodiments described are not limited to the specific component parts herein named. For example the articulating components could be made from a series of gears and/or wheels that are configured to articulate a basket. Additionally, not all component parts are necessary, nor is it required that the component parts be assembled in an identical fashion. For example, the locations of lever 154 and slide 152 are not limited to that which is shown; both may be placed in alternate locations including the side of the retrieval device as depicted in FIG. 18, retrieval device 170. Additionally, wire pivots 153a, 153b may be configured so as to move along the same female thread 156a, as depicted in FIG. 18.

To use a retrieval device having an articulating basket for removing an object from a patient that is configured for simultaneous basket extension or basket retraction, the basket is inserted into the patient and is moved near an item to be removed from a patient, i.e. a calculus, stone, etc. The basket is extended out to the object to be removed. The object to be removed is captured by simultaneously articulating the basket while extending or retracting the basket until the object is captured. The basket is then retracted and the device and object are removed from the patient.

As is evident, the embodiments provide a very effective solution for removal of stones, calculi, or other objects from a patient by a device that allows for simultaneous basket articulation and extension, and also provides for simultaneous basket articulation and retraction.

The foregoing description and drawings are provided for illustrative purposes only and are not intended to limit the scope of the invention described herein or with regard to the details of its construction and manner of operation. It will be evident to one skilled in the art that modifications and variations may be made without departing from the spirit and scope of the invention. Changes in form and in the proportion of parts, as well as the substitution of equivalence, are contemplated as circumstances may suggest and render expedience; although specific terms have been employed, they are intended in a generic and descriptive sense only and not for the purpose of limiting the scope of the invention set forth in the following claims.

What is claimed is:

1. A medical device, the device comprising:
   a body having a longitudinal axis;
   an articulator movably connected to the body, the articulator comprising two ergonomically-shaped finger holes and a thumb hole;
   at least a first wire and a second wire having distal ends;
   the first wire and the second wire in communication with the articulator;
   a tool formed by the distal ends of the first wire and the second wire, wherein the articulator is capable of moving the tool outside a longitudinal plane and along a transverse axis; and
   a pair of springs within the body and in communication with the articulator and the body,
   wherein the tool is capable of being extended and retracted in the longitudinal plane while simultaneously moving outside the longitudinal plane, and wherein the articulator is disposed about an external surface of the body.

2. The device according to claim 1 wherein the tool is a basket, a grasping device, or a sampling device.

3. The device according to claim 1 wherein the articulator is movably connected to the body via a pivot pin.

4. The device according to claim 1 wherein the articulator further comprises at least a first pivot pin and a second pivot pin, wherein at least one wire is in communication with the first pivot pin or the second pivot pin.

5. The device according to claim 1 wherein the articulator further comprises at least a first pivot pin and a second pivot pin, wherein the first wire and the second wire are in communication with the first pivot pin and the second pivot pin.

6. The device according to claim 1 wherein the articulator further comprises a first pivot pin, a second pivot pint, and a third pivot pin; wherein the first wire is connected to the first pivot pin and the second pivot pin, and the second wire is connected to the third pivot pin.

7. The device according to claim 1 further comprising a wire connection point; wherein the distal ends of the first wire and the second wire are connected via a soldered point, a loop, or a connection disk.

8. The device according to claim 1 wherein the body further comprises an axis where along the articulator can move in a proximal direction and a distal direction.

9. The device according to claim 1 wherein the first wire and the second wire further comprise wire fibers and the wire fibers are in a net-configuration.

10. A medical device, the device comprising:
a body having a longitudinal axis;
an articulator movably connected to the body, the articulator comprising two ergonomically-shaped finger holes and a thumb hole and at least a first pivot pin and a second pivot pin, wherein a first wire and a second wire are in communication with the first pivot pin and the second pivot pin;
at least the first wire and the second wire having distal ends;
the first wire and the second wire in communication with the articulator;
a sheath at least partially disposed about the first wire and the second wire;
a tool formed by the distal end of the first wire and the second wire, wherein the articulator is capable of moving the tool outside a longitudinal plane; and
a pair of springs within the body and in communication with the articulator and the body,
wherein the tool is capable of being extended and retracted in the longitudinal plane while simultaneously moving outside the longitudinal plane and along a transverse axis, wherein the articulator is disposed about an external surface of the body.

11. The device according to claim 10 further comprising a wire connection point; wherein the distal ends of the first wire and the second wire are connected via a soldered point, a loop, or a connection disk.

* * * * *